(12) United States Patent
Konosu et al.

(10) Patent No.: US 6,337,403 B1
(45) Date of Patent: Jan. 8, 2002

(54) TRIAZOLE DERIVATIVES HAVING ANTIFUNGAL ACTIVITY

(75) Inventors: Toshiyuki Konosu, Kawasaki; Sadao Oida, Yokohama; Makoto Mori, Ohmiya; Takuya Uchida, Tokyo; Satoshi Ohya, Tokyo; Akihiko Nakagawa, Tokyo, all of (JP)

(73) Assignee: Sankyo Company, Limited, Tokyo (JP)

(*) Notice: Subject to any disclaimer, the term of this patent is extended or adjusted under 35 U.S.C. 154(b) by 0 days.

(21) Appl. No.: 09/872,744

(22) Filed: Jun. 1, 2001

Related U.S. Application Data

(62) Division of application No. 09/656,154, filed on Sep. 6, 2000.

(30) Foreign Application Priority Data

Sep. 9, 1999 (JP) .......................................... 11-255702
Apr. 5, 2000 (JP) .......................................... 12-103826

(51) Int. Cl.⁷ ..................... A61K 31/4196; A61P 31/00
(52) U.S. Cl. ..................................... 548/383; 548/267.4
(58) Field of Search ........................ 548/267.4; 514/383

(56) References Cited

U.S. PATENT DOCUMENTS

| | | | |
|---|---|---|---|
| 4,483,863 A | 11/1984 | Richardson et al. | |
| 4,727,159 A | 2/1988 | Richardson et al. | |
| 5,393,769 A | 2/1995 | Oida et al. | |
| 5,489,606 A | * 2/1996 | Oida et al. ................... | 514/383 |
| 5,773,443 A | * 6/1998 | Ray et al. .................. | 548/267.4 |
| 5,945,438 A | * 8/1999 | Tokizawa et al. ........... | 514/383 |
| 5,977,152 A | 11/1999 | Oida et al. | |

FOREIGN PATENT DOCUMENTS

| | | |
|---|---|---|
| EP | 0 841 327 A | 5/1998 |
| EP | 1000951 A | 5/2000 |
| JP | 8-333350 A | 12/1996 |
| JP | 10-158167 A | 6/1998 |
| JP | 11-80135 A | 3/1999 |
| WO | WO 98/33778 | 8/1998 |
| WO | WO 99/02524 | 1/1999 |

OTHER PUBLICATIONS

S. Oida, et al, "Synthesis and Antifungal Activities of R–102557 and Related Dioxane–Triazole Derivatives", *Chem. Pharm. Bull.*, 48(5), 694–707, May 2000.

\* cited by examiner

*Primary Examiner*—Robert W. Ramsuer
*Assistant Examiner*—Golam M. M. Shameem
(74) *Attorney, Agent, or Firm*—Frishauf, Holtz, Goodman, Langer & Chick, P.C.

(57) ABSTRACT

Compounds of the following formula (I) and pharmaceutically acceptable esters and salts thereof:

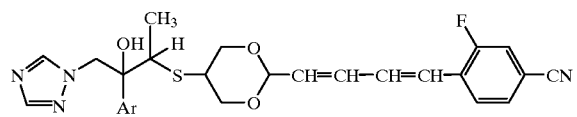

Ar is a phenyl group which may optionally be substituted by from 1 to 3 substituents selected from the group consisting of halogen atoms and trifluoromethyl groups. The compounds (and pharmaceutically acceptable esters and salts thereof) have excellent antifungal activity.

16 Claims, 2 Drawing Sheets

TRIAZOLE DERIVATIVES HAVING ANTIFUNGAL ACTIVITY

This application is a divisional of Ser. No. 09/656,154 Sep. 6, 2000.

TECHNICAL FIELD

The present invention relates to triazole derivatives having excellent activity against a wide range of fungi, to certain of said derivatives in crystalline form, to a pharmaceutical composition containing said derivatives, to a method of treating and preventing fungal infections using said derivatives and to an intermediate useful in the preparation of said derivatives.

BACKGROUND OF THE INVENTION

Antifungal triazole derivatives having the following general formula are disclosed in Japanese Patent Application (Kokai) Hei 8-333350 and EP-A-0841327:

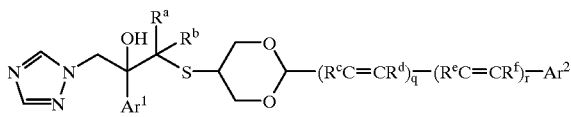

wherein $R^a$ represents a hydrogen atom or an alkyl group, $R^b$ represents an alkyl group, $Ar^1$ and $Ar^2$ can each represent an optionally substituted phenyl group, q and r can each represent 1, and each of $R^c$, $R^d$, $R^e$ and $R^f$ can represent a hydrogen atom. Similar compounds, in which the sulfur atom is replaced by a methylene group are disclosed in Japanese Patent Application (Kokai) Hei 11-80135 and WO-A-99/02524.

These prior art compounds show good antifungal activity. There is, however, a need for further compounds having improved antifungal activity, stability, pharmacokinetics and safety.

BRIEF SUMMARY OF THE INVENTION

It is therefore an object of the present invention to provide a series of new compounds having antifungal activity.

Other objects and advantages of the present invention will become apparent as the description proceeds.

The compounds of the present invention are compounds of the following formula (I), and pharmaceutically acceptable salts and ester derivatives thereof:

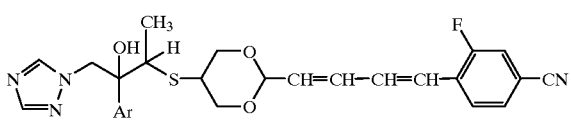

wherein Ar is a phenyl group which may optionally be substituted by from 1 to 3 substituents selected from the group consisting of halogen atoms and trifluoromethyl groups.

The present invention also provides the compound (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol [formula (Ib) below] in crystalline form:

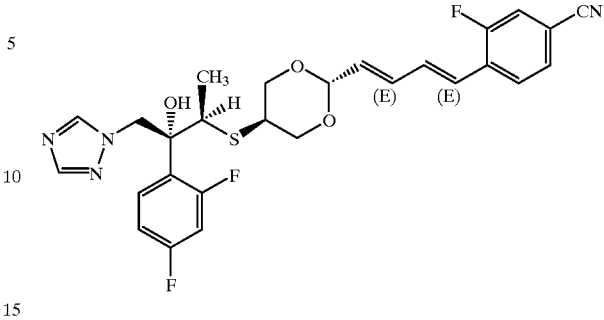

The present invention also provides a pharmaceutical composition comprising an effective amount of a pharmacologically active compound together with a pharmaceutically acceptable carrier therefor, wherein said pharmacologically active compound is a compound of formula (I) or a pharmaceutically acceptable salt or ester derivative thereof.

The present invention also provides a method for the prophylaxis or treatment of fungal infections in a mammal, which may be a human, which comprises administering to said mammal an effective amount of a compound having antifungal activity, wherein said compound having antifungal activity is a compound of formula (I) or a pharmaceutically acceptable salt or ester derivative thereof.

DETAILED DESCRIPTION OF THE INVENTION

Figure 1:
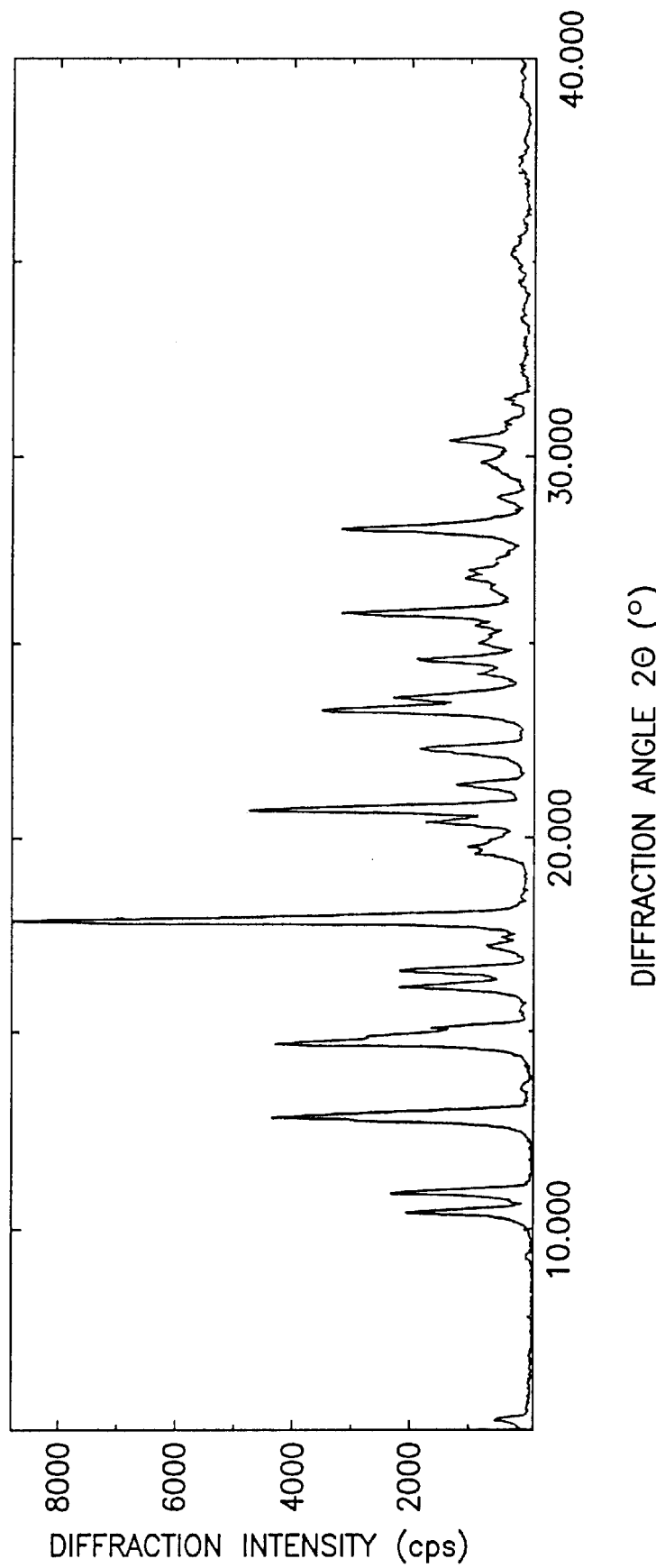
FIG. 1 shows the X-ray diffraction pattern of a first crystalline form of (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol, by the powder method using the copper $K_\alpha$-ray, $\lambda=1.54$ Å. The vertical axis of the powder X-ray diffraction pattern indicates diffraction intensity in units of counts/second (cps), while the horizontal axis indicates the diffraction angle as the value 2θ.

Examples of the halogen atoms which are optional substituents on the group Ar include fluorine, chlorine and bromine atoms. Fluorine and chlorine atoms are preferred, and fluorine atoms are most preferred.

Examples of the substituent Ar include phenyl, dichlorophenyl, difluorophenyl, dibromophenyl, chlorophenyl, fluorophenyl, bromophenyl, trifluorophenyl, trichlorophenyl, tribromophenyl, (trifluoromethyl)phenyl, bis(trifluoromethyl)phenyl, tris(trifluoromethyl)phenyl, fluoro(trifluoromethyl)phenyl and chloro(trifluoromethyl)phenyl groups. Preferably, the group Ar is a phenyl group which is substituted by 1 or 2 substituents selected from fluorine atoms, chlorine atoms and trifluoromethyl groups.

More preferably, the substituent Ar is a phenyl group which is substituted with 1 or 2 fluorine atom(s). Still more preferably, the substituent Ar is a 2-fluorophenyl, 4-fluorophenyl, 2,3-difluorophenyl, 2,4-difluorophenyl or 2,5-difluorophenyl group, particularly a 2-fluorophenyl or 2,4-difluorophenyl group. Most preferably, the substituent Ar is a 2,4-difluorophenyl group.

The compounds of formula (I) of the present invention can exist in the form of stereoisomers and geometrical isomers. There are two asymmetric carbon atoms in the compounds of formula (I) and each of said carbon atoms can therefore take the R or S configuration. Preferably both of them are R configuration. These optical isomers can be isolated by a conventional optical resolution method. Each of the four possible optical isomers for any given compound of formula (I) can be prepared by asymmetric synthesis. These optical isomers can also be isolated by conventional techniques such as fractional crystallization and chromatography.

The compounds of formula (I) have a 2,5-disubstituted-1,3-dioxane ring. Consequently, they can exist as cis or trans isomers with regard to the 2- and 5-positions. The trans isomers are preferred. These cis and trans isomers can be isolated by conventional techniques such as fractional crystallization and chromatography.

The compounds of formula (I) have two double bonds. Consequently, they exist as geometrical isomers in which each double bond has either the E or Z configuration. The preferred geometrical isomers are those in which both of the double bonds are E configuration. These geometrical isomers can be isolated by conventional techniques such as fractional crystallization and chromatography.

The present invention includes each of the individual isomers described above and mixtures of two or more thereof in any proportion, including racemic mixtures.

Of the possible isomers of the compounds of formula (I), the following isomer of formula (Ia) is most preferred:

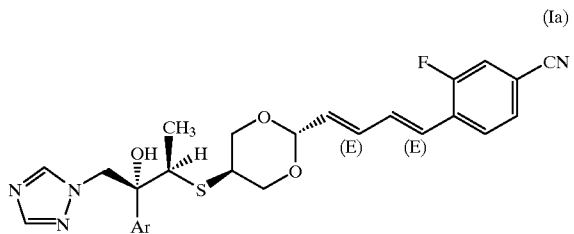

The present invention encompasses pharmaceutically acceptable ester derivatives of the compounds of formula (I). These pharmaceutically acceptable ester derivatives are so-called pro-drugs, in which a functional group (the hydroxy group) in the compound of formula (I) is protected by a group which is capable of being cleaved by a chemical or biological process (e.g. by hydrolysis) on administration of the derivative to the body of a live animal to give the parent compound of formula (I) or a salt thereof. Whether a derivative of a compound of formula (I) is pharmaceutically acceptable can be easily determined. The ester derivative under investigation is administered orally or intravenously to a test animal such as a mouse or a rat and the body fluids of the test animal are thereafter studied. If the parent compound of formula (I) or a salt thereof is detected in the body fluids of the test animal, the ester derivative under investigation is judged to be a pharmaceutically acceptable ester derivative of the compound of formula (I).

The group in the compounds of formula (I) which can be modified to give a pharmaceutically acceptable ester derivative thereof is the hydroxyl group. Thus, the pharmaceutically acceptable ester derivatives of the compounds of formula (I) are those in which the hydroxyl group is protected to give an ester derivative which is capable of being cleaved in the body of a live animal to give the parent compound of formula (I) or a salt thereof.

Examples of pharmaceutically acceptable ester derivatives of the compounds of formula (I) are those in which the hydroxy group is protected by an acyl group. Examples of said acyl groups include aliphatic acyl groups, aromatic acyl groups, alkoxycarbonyl groups, aralkyloxycarbonyl groups, aminoacyl groups and posphoric acid groups.

The aliphatic acyl groups have from 1 to 20 carbon atoms and can contain from 1 to 3 double or triple bonds. Examples of such aliphatic acyl groups include alkylcarbonyl groups having from 1 to 20 carbon atoms, alkenylcarbonyl groups having from 3 to 20 carbon atoms and alkynylcarbonyl groups having from 3 to 20 carbon atoms, said groups optionally being substituted by at least one substituent such as a hydroxy group, an alkoxy group, a halogen atom, an alkanoyloxy group, a phosphoric acid group, a carboxy group, and an alkoxycarbonyl group.

Examples of the alkylcarbonyl groups having from 1 to 20 carbon atoms include formyl, acetyl, propionyl, butyryl, isobutyryl, pivaloyl, valeryl, isovaleryl, octanoyl, nonanoyl, decanoyl, 3-methylnonanoyl, 8-methyl-nonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methyl-hexadecanoyl, octadecanoyl, 1-methylheptadecanoyl, nonadecanoyl, and eicosanoyl groups.

Examples of the alkenylcarbonyl groups having from 3 to 20 carbon atoms include acryloyl, methacryloyl, crotonoyl, isocrotonoyl and (E)-2-methyl-2-butenoyl groups.

Examples of the alkynylcarbonyl groups having from 3 to 20 carbon atoms include propioloyl groups.

The aromatic acyl groups are arylcarbonyl groups having from 7 to 11 carbon atoms such as benzoyl, α-naphthoyl and β-naphthoyl groups. The aryl ring of these aromatic acyl groups may optionally have at least one substituent such as an alkyl group having from 1 to 4 carbon atoms, an aromatic acyl group (which may optionally have at least one substituent such as an alkyl group having from 1 to 4 carbon atoms), a halogen atom, an alkoxy group having from 1 to 4 carbon atoms, a hydroxy group, a carboxy group, an alkoxycarbonyl group wherein the alkoxy moiety has from 1 to 4 carbon atoms, a hydroxyalkyl group having from 1 to 4 carbon atoms, an alkyl group having from 1 to 4 carbon atoms which is substituted by a phosphoric acid group, an alkanoyloxyalkyl group in which the alkyl moiety has 1 to 4 carbon atoms or an alkyl group having from 1 to 4 carbon atoms which is substituted by a carboxy group.

The alkoxycarbonyl groups comprise a carbonyl group whch is substituted by an alkoxy group having from 1 to 20 carbon atoms, examples of which include groups such as methoxycarbonyl, ethoxycarbonyl, isobutoxycarbonyl and tert-butoxycarbonyl groups. The alkoxy moiety of these alkoxycarbonyl groups may optionally have at least one substituent such as an alkyl group having from 1 to 4 carbon atoms, a halogen atom, an alkoxy group having from 1 to 4 carbon atoms, a hydroxy group, an alkanoyloxy group, a phosphoric acid group, a carboxy group, an alkoxycarbonyl group in which the alkoxy moiety has from 1 to 4 carbon atoms, a hydroxyalkyl group having from 1 to 4 carbon atoms, an alkyl group having from 1 to 4 carbon atoms which is substituted by a phosphoric acid group or an alkyl group having from 1 to 4 carbon atoms which is substituted by a carboxy group.

The aralkyloxycarbonyl groups comprise a carbonyl group which is substituted by an aralkyloxy group having from 8 to 20 carbon atoms, examples of which include a benzyloxycarbonyl group. The aryl ring of these aralkyloxycarbonyl groups may optionally have at least one substituent such as an alkyl group having from 1 to 4 carbon atoms, a halogen atom, an alkoxy group having from 1 to 4 carbon atoms, a hydroxy group, a phosphoric acid group, a carboxy group, an alkoxycarbonyl group in which the alkoxy moiety has from 1 to 4 carbon atoms, a hydroxyalkyl group having from 1 to 4 carbon atoms, an alkyl group having from 1 to 4 carbon atoms which is substituted by a phosphoric acid group or an alkyl group having from 1 to 4 carbon atoms which is subtituted by a carboxy group.

The amino acyl group is an amino acid group such as glycyl, alanyl, leucyl, phenylalanyl, glutamyl and asparaginyl groups or an aminoalkanoyl group having from 1 to 10 carbon atoms such as β-alanyl, aminobutyryl and aminooctanoyl groups.

The phosporic acid group includes a phosporic acid group; a monoalkyl-phosphonic acid group in which the alkyl moiety has from 1 to 20 carbon atoms, examples of which include methylphosphate, ethyl phosphate, propyl phosphate, butyl phosphate decyl phosphate and octadecyl phosphate groups; and a dialkylphosphonic acid group in which each alkyl moiety is the same or different and has from 1 to 20 carbons atoms, examples of which include dimethyl phosphate, diethyl phosphate, dipropyl phosphate, dibutyl phosphate, didecyl phosphate and dioctadecyl phosphate groups.

A pharmaceutically acceptable salt of a compound of formula (I) or a pharmaceutically acceptable ester derivative thereof is a salt which has the same low toxicity as, or is not significantly more toxic than, the compound of formula (I) or pharmaceutically acceptable derivative thereof and which has the same, or not significantly lower, pharmacological activity.

The compounds of formula (I) and pharmaceutically acceptable ester derivatives thereof have a basic triazole group and can, optionally, have aminoacyl groups and they can therefore form acid addition salts. Examples of such salts include inorganic acid salts, for example hydrochlorides, hydrobromides, sulfates and nitrates; carboxylic acid salts, for example acetates, fumarates, maleates, oxalates, malonates, succinates, citrates and malates; sulfonates, for example methane-sulfonates, ethanesulfonates, benzenesulfonates and toluenesulfonates; and amino acid salts, for example glutamates and aspartates. Inorganic acid salts and carboxylic acid salts are preferred, and hydrochlorides, nitrates, fumarates, maleates and oxalates are most preferred.

The pharmaceutically acceptable ester derivatives of the compounds of formula (I) may contain a phosphoric acid group or a carboxy group and can, therefore, form salts with a base. Examples of such salts include alkali metal salts, for example sodium, potassium and lithium salts; alkaline earth metal salts, for example calcium and magnesium salts; other inorganic salts, for example ammonium salts; amine salts, for example t-octylamine, dibenzylamine, morpholine, glucosamine, phenylglycine alkyl esters, ethylenediamine, methylglucamine, guanidine, diethylamine, triethylamine, dicyclohexylamine, N,N'-dibenzylethylenediamine, chloroprocaine, procaine, diethanolamine, benzylphenethylamine, piperazine, tetramethylammonium and tris (hydroxymethyl)aminomethane salts.

Therefore, reference to "a compound of the formula (I) or a pharmaceutically acceptable ester or salt thereof" means a compound of the formula (I), or a pharmaceutically acceptable (i) salt or (ii) ester of said compound or (iii) a salt of an ester of said compound. Reference to "or a pharmaceutically acceptable ester or salt thereof" following a named compound or a reference to a compound of a specified formula, similarly means a pharmaceutically acceptable (i) salt or (ii) ester of said compound or (iii) a salt of an ester of said compound.

When a compound of formula (I) or a pharmaceutically acceptable ester or salt thereof is allowed to stand so that it is open to the atmosphere, it may absorb water to form a hydrate. A compound of formula (a) or a pharmaceutically acceptable ester or salt thereof may also absorb a solvent to give a solvate. The compounds of the present invention as defined herein also encompasses these hydrates and solvates.

The compound of formula (Ib) in crystalline form of the present invention is a solid which has a regular arrangement of atoms (groups of atoms) in a three-dimensional structure and repeats the arrangement. The crystal is different from an amorphous solid that has no regular arrangement of atoms in a three-dimensional structure.

Different crystalline forms of the compound of formula (Ib) of the present invention can be produced depending upon the crystallization conditions used. These different crystalline forms have different three-dimensional arrangements of the atoms and have different physicochemical properties.

The present invention encompasses these different crystalline forms and mixtures of two or more of said crystalline forms.

One example of the compound of formula (Ib) in crystalline form is a crystalline form which has main peaks at lattice distances of 3.14, 3.39, 3.71, 3.75, 4.21, 4.88, 5.28, 5.42, 5.89, 5.95, 6.79, 6.86, 8.03 and 8.41 Å determined by X-ray diffraction by the powder method using the copper $K_\alpha$-ray, $\lambda=1.54$ Å. A second example of the compound of formula (Ib) in crystalline form is a crystalline form which has main peaks at lattice distances of 3.62, 3.96, 4.54, 4.59, 4.79, 4.91, 5.32, 5.48, 6.18, 7.99 and 15.93 Å determined by X-ray diffraction by the powder method using the copper $K_\alpha$-ray, $\lambda=1.54$ Å. The main peaks are those having a diffraction intensity of greater than 2000 counts per second (cps).

Preferred compounds of formula (I) and pharmaceutically acceptable salts and ester derivatives thereof include:

(A) a compound of formula (I) or a pharmaceutically acceptable salt or ester derivative thereof wherein Ar represents a 2,4-difluorophenyl group or a 2-fluorophenyl group.

(B) a compound of formula (I) or a pharmaceutically acceptable salt or ester derivative thereof wherein Ar is a 2,4-difluorophenyl group.

(C) a compound of formula (Ia) below or a pharmaceutically acceptable salt or ester derivative thereof:

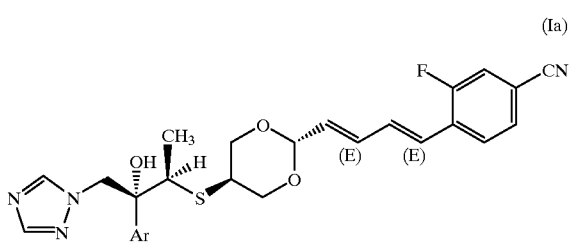

(Ia)

wherein Ar is a phenyl group or a phenyl group substituted with 1 to 3 substituents selected from halogen atoms and trifluoromethyl groups.

(D) (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol (compound (Ib)) or a pharmaceutically acceptable salt or ester derivative thereof.

More preferred are the following compounds of formula (I) and pharmaceutically acceptable salts or ester derivatives thereof:

(2R,3R)-3-[[trans-2-[(1E,3E)-4-(4-cyano-2-fluorophenyl)-1,3-butadien-1-yl]-1,3-dioxan-5-yl]thio]-2-(2-fluorophenyl)-1-(1H-1,2,4-triazol-1-yl)-2-butanol, (2R,3R)-3-[[trans-2-[(1E,3E)-4-(4-cyano-2-fluorophenyl)-1,3-butadien-1-yl]-1,3-dioxan-5-yl]thio]-2-(4-fluorophenyl)-1-(1H-1,2,4-triazol-1-yl)-2-butanol, (2R,3R)-3-[[trans-2-[(1E,3E)-4-(4-cyano-2-fluorophenyl)-1,3-butadien-1-yl]-1,3-dioxan-5-yl]thio]-2-(2,3-difluorophenyl)-1-(1H-1,2,4-triazol-1-yl)-2-butanol, (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol, (2R,3R)-3-[[trans-2-[(1E,3E)-4-(4-cyano-2-fluorophenyl)-1,3-butadien-1-yl]-1,3-dioxan-5-yl]thio]-2-(2,5-difluorophenyl)-1-(1H-1,2,4-triazol-1-yl)-2-butanol, (2R,3R)-3-[[trans-2-[(1E,3E)-4-(4-cyano-2-fluorophenyl)-1,3-butadien-1-yl]-1,3-dioxan-5-yl]thio]-2-(4-chlorophenyl)-1-(1H-1,2,4-triazol-1-yl)-2-butanol, (2R,3R)-3-[[trans-2-[(1E,3E)-4-(4-cyano-2-fluorophenyl)-1,3-butadien-1-yl]-1,3-dioxan-5-yl]thio]-2-(2,4-dichlorophenyl)-1-(1H-1,2,4-triazol-1-yl)-2-butanol, and (2R,3R)-3-[[trans-2-[(1E,3E)-4-(4-cyano-2-fluorophenyl)-1,3-butadien-1-yl]-1,3-dioxan-5-yl]thio]-2-[4-(trifluoromethyl)phenyl]-1-(1H-1,2,4-triazol-1-yl)-2-butanol.

Yet more preferred are the following compounds of formula (I) and pharmaceutically acceptable salts and ester derivatives thereof:

(2R,3R)-3-[[trans-2-[(1E,3E)-4-(4-cyano-2-fluorophenyl)-1,3-butadien-1-yl]-1,3-dioxan-5-yl]thio]-2-(2-fluorophenyl)-1-(1H-1,2,4-triazol-1-yl)-2-butanol, (2R,3R)-3-[[trans-2-[(1E,3E)-4-(4-cyano-2-fluorophenyl)-1,3-butadien-1-yl]-1,3-dioxan-5-yl]thio]-2-(4-fluorophenyl)-1-(1H-1,2,4-triazol-1-yl)-2-butanol, (2R,3R)-3-[[trans-2-[(1E,3E)-4-(4-cyano-2-fluorophenyl)-1,3-butadien-1-yl]-1,3-dioxan-5-yl]thio]-2-(2,3-difluorophenyl)-1-(1H-1,2,4-triazol-1-yl)-2-butanol, (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol, and (2R,3R)-3-[[trans-2-[(1E,3E)-4-(4-cyano-2-fluorophenyl)-1,3-butadien-1-yl]-1,3-dioxan-5-yl]thio]-2-(2,5-difluorophenyl)-1-(1H-1,2,4-triazol-1-yl)-2-butanol.

The most preferred compound of formula (I) is (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol.

Compounds of formula (I) can be prepared by method A illustrated below.

Method A

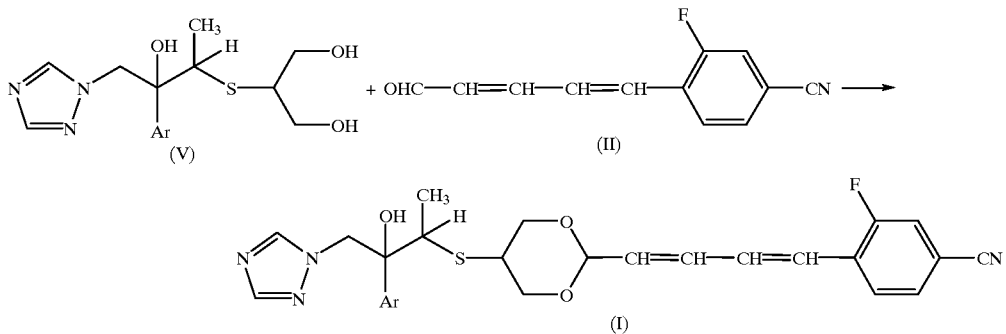

In the above reaction scheme, the substituent Ar is as defined earlier.

The method A comprises the reaction of a compound of formula (V) with a compound of formula (II) in the presence of an acetalization reagent in an inert solvent, water produced during this reaction being removed from the reaction mixture during said reaction.

In method A, a salt of the compound of formula (V) or the following compound of formula (Va), can be used instead of the compound of formula (V) as the starting material:

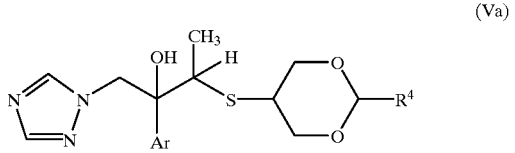

(Va)

wherein Ar is as defined above, and $R^4$ is an alkyl group having from 1 to 6 carbon atoms an aryl group having from 6 to 10 carbon atoms or an indenyl group.

In the definition of substituent $R^4$, the alkyl group having from 1 to 6 carbon atoms is a straight or branched alkyl group having from 1 to 6 carbon atoms, examples of which include methyl, ethyl, propyl, isopropyl, butyl, isobutyl, sec-butyl, tert-butyl, pentyl and hexyl groups. Straight or branched alkyl groups having from 1 to 4 carbon atoms are preferred. In the definition of substituent $R^4$, the aryl group having from 6 to 10 carbon atoms is an aromatic hydrocarbon group having from 6 to 10 carbon atoms such as a phenyl or naphthyl group, of which phenyl groups are preferred. Compounds of formula (Va) in which $R^4$ is a phenyl group are preferred.

Compounds of formula (V) can be prepared according to the method described in Japanese Patent Application (Kokai) Hei 8-333350, or by a modified version thereof. Compounds of formula (Va) can be obtained as an intermediate in the process for preparing the compounds of formula (V) described in Japanese Patent Application (Kokai) Hei 8-333350. Salts of the compounds of formula (V) can be obtained by the removal of the acetal protecting group from the compounds of formula (Va) using an acid.

In method A, an acetal derivative of the compound of formula (II) can be used as an alternative starting material to the compound of formula (II). The compound of formula (II) can be prepared by Method B described below, while the acetal derivative of the compound of formula (II) can be obtained by using as the starting material in method B an acetal derivative of the compound of formula (IV).

In method A, the amount of the compound of formula (II) or acetal derivative thereof which is used is from 0.5 to 2 molar equivalents of the compound of formula (V), and is preferably from 0.9 to 1.2 molar equivalents.

In method A, there is no particular limitation on the solvent used provided that it has no adverse effect on the reaction and that it dissolves the starting materials at least to some extent. Suitable solvents are aprotic solvents for example halogenated hydrocarbons such as dichloromethane, chloroform or 1,2-dichloroethane; aromatic hydrocarbons such as benzene, toluene or xylene; ethers such as diethyl ether or tetrahydrofuran; or a mixture thereof. Halogenated hydrocarbons and ethers are preferred, and dichloromethane or tetrahydrofuran are particularly preferred.

In method A, examples of suitable acetalization reagents include inorganic acids such as hydrogen chloride, sulfuric acid or nitric acid; Lewis acids such as boron trifluoride, zinc chloride, magnesium bromide, titanium tetrachloride or aluminum chloride; sulfonic acids such as methanesulfonic acid, benzenesulfonic acid, p-toluenesulfonic acid, camphorsulfonic acid or trifloromethanesulfonic acid; carboxylic acids such as formic acid, acetic acid, trifluoroacetic acid, oxalic acid or citric acid; and silylating agents such as chlorotrimethylsilane or trimethylsilyl trifluoromethanesulfonate. The preferred acetalization reagents are sulfonic acid derivatives, and p-toluenesulfonic acid is particularly preferred.

In method A, the amount of the acetalization reagent used is from 0.5 to 3 molar equivalents of the amount of the compound of formula (V) used, and is preferably from 1.0 to 1.4 molar equivalents.

Water produced during the reaction of Method A can be removed by azeotropic distillation of the reaction solvent, by evaporation under reduced pressure or by using a dehydrating reagent such as molecular sieves.

The reaction temperature employed in the reaction of method A depends upon various factors such as the solvent, the starting materials and the acetalization reagent used. However, it is usually from 0° C. to the boiling point of the solvent used, and is preferably from 5° C. to 40° C.

The reaction time for the reaction of method A depends on a number of factors such as the starting materials, the acetalization reagent, the solvent and the reaction temperature. However, it is usually from 0.5 to 24 hours, and is preferably from 1 to 5 hours.

After the reaction of method A is complete, the reaction mixture is neutralized with an aqueous sodium bicarbonate solution or the like and the desired compound is then isolated using a conventional isolation technique. For example, the reaction mixture or the residue of the reaction mixture obtained by evaporation of the solvent from the reaction mixture is partitioned between an organic solvent and water, washing the organic layer with water and then distilling off the solvent to give the desired product of formula (I).

The product thus obtained can, if necessary, be further purified using a conventional technique such as recrystallization, reprecipitation or chromatography.

A pharmaceutically acceptable ester derivative of a compound of formula (I) can be prepared in a conventional manner known to those skilled in the art (see, for example, "Protective Groups in Organic Synthesis", Theodora W. Greene and Peter G. M. Wuts, Second Edition, 1991, John Wiley & Sons, Inc.). Of these pharmaceutically acceptable ester derivatives, acyl derivatives are prepared by acylation of the hydroxy group according to procedures well known in the art.

The compound of formula (I) or ester derivative thereof thus obtained can be converted to a salt thereof by the addition of a pharmaceutically acceptable acid or base to a solution of said compound of formula (I) or ester derivative thereof.

The solvent used in preparing a salt of a compound of formula (I) or a pharmaceutically acceptable ester derivative thereof is not particularly limited provided that it has no adverse effect on the reaction and that it dissolves the starting materials at least to some extent. Examples of suitable solvents include aromatic hydrocarbons such as benzene or toluene; halogenated hydrocarbons such as dichloromethane or chloroform; ethers such as diethyl ether, tetrahydrofuran or dioxane; esters such as ethyl acetate; alcohols such as methanol or ethanol; ketones such as acetone; nitriles such as acetonitrile; hydrocarbons such as hexane or cyclohexane; or a mixture thereof.

The acid for preparing the pharmaceutically acceptable salt may be a pharmaceutically acceptable acid, for example inorganic acids such as hydrochloric acid, hydrogen bromide, sulfuric acid or nitric acid; carboxylic acids such acetic acid, fumaric acid, maleic acid, oxalic acid, malonic acid, succinic acid, citric acid or malic acid; sulfonic acids such as methanesulfonic acid, ethanesulfonic acid, benzenesulfonic acid or toluenesulfonic acid; and amino acid derivatives such as glutamic acid or aspartic acid. Inorganic acids and carboxylic acids are preferred, and hydrochloric acid, nitric acid, fumaric acid, maleic acid or oxalic acid are particularly preferred.

The base for preparing the pharmaceutically acceptable salt may be a pharmaceutically acceptable base, for example alkali metal hydroxides or alkaline earth metal hydroxides such as sodium hydroxide, potassium hydroxide, lithium hydroxide, calcium hydroxide or magnesium hydroxide; alkaline metal carbonates or alkaline earth metal carbonates such as sodium carbonate, potassium carbonate, lithium carbonate, calcium carbonate or magnesium carbonate; alkali metal hydrogencarbonates such as sodium hydrogencarbonate, potassium hydrogencarbonate or lithium hydrogencarbonate; other inorganic bases such as ammonia; and amine salts such as t-octylamine, dibenzylamine, morpholine, glucosamine, phenylglycine alkyl esters, ethylenediamine, methylglucamine, guanidine, diethylamine, triethylamine, dicyclohexylamine, N,N'-dibenzylethyl-enediamine, chloroprocaine, procaine, diethanolamine, benzylphenethylamine, piperazine, tetramethylammonium and tris(hydroxymethyl)aminomethane.

The desired salt of the compound of formula (I) or pharmaceutically acceptable ester derivative thereof is usually precipitated as crystals or a powder from the reaction solution of said compound of formula (I) or pharmaceutically acceptable derivative thereof with an acid or base. The desired salt can also be obtained as a precipitate by the addition of a solvent which slightly dissolves the salt to the solution of said salt, or by removal of the solvent from the solution containing the desired salt.

The compound of formula (II) or an acetal derivative thereof is particularly suitable for the synthesis of the compounds of formula (I) of the present invention and it therefore also forms a part of the present invention. The following compound of formula (IIa) or an acetal derivative thereof is particularly preferred.

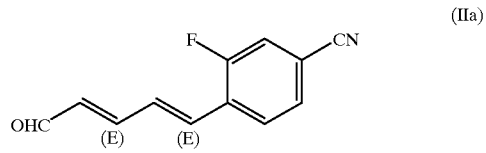

(IIa)

An acetal derivative of the compound of formula (II) or the compound of formula (IIa) is a derivative in which the aldehyde group of said compound of formula (II) or said compound of formula (IIa) is protected as a group of formula $CH(OR^1)(OR^2)$ wherein $R^1$ and $R^2$ are the same or different and each is independently selected from the group consisting of hydrogen atoms and alkyl groups having from 1 to 4 carbon atoms, or $R^1$ and $R^2$ together form an alkylene group having from 1 to 4 carbon atoms.

In the definition of the substituents $R^1$ and $R^2$ the alkyl groups having from 1 to 4 carbon atoms include methyl, ethyl, propyl, isopropyl, butyl, isobutyl, sec-butyl and tert-butyl groups, of which methyl groups are preferred.

In the definition of the substituents $R^1$ and $R^2$, the alkylene groups having from 1 to 4 carbon atoms include methylene, methylmethylene, ethylene, propylene, trimethylene, tetramethylene, 1-methyltrimethylene, 2-methyltrimethylene and 3-methyltrimethylene groups, of which ethylene groups are preferred.

The preferred acetal derivatives of the compounds of formulae (II) and (IIa) are those having the acetal group $-CH(OR^1)(OR^2)$ in which each of $R^1$ and $R^2$ is a methyl group.

The compound of formula (II) and the acetal derivatives thereof have two double bonds and they can therefore exist as geometrical isomers in which each double bond as the E or Z configuration. The present invention encompasses both the individual geometrical isomers and mixtures of two or more of them. Among these isomers, the compound of formula (IIa) and acetal derivatives thereof in which both double bonds have the E configuration is preferred.

When the compound of formula (II) or an acetal derivative thereof is allowed to stand so that it is open to the atmosphere, it may absorb water to form a hydrate. The compound of formula (II) or an acetal derivative thereof may also absorb a solvent to give a solvate. The present invention also encompasses these hydrates and solvates.

The starting material of formula (II) can be prepared by Method B depicted in the reaction scheme shown below.

Method B

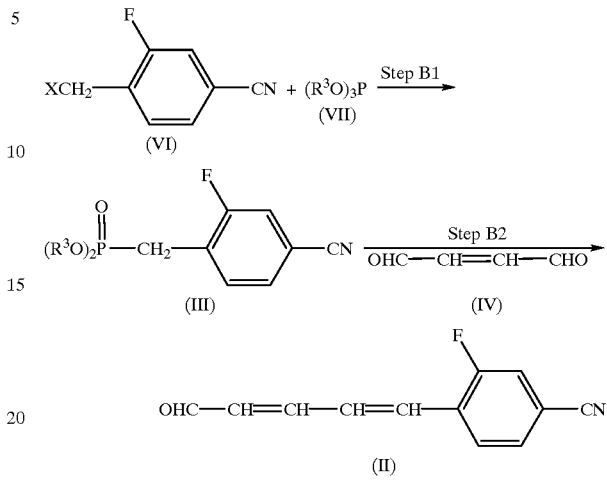

In the above reaction scheme, X is a halogen atom (preferably a chlorine or bromine atom) and $R^3$ is an alkyl group having from 1 to 6 carbon atoms which may optionally be substituted with at least one fluorine atom.

Method B involves the reaction of a 4-(halogenomethyl)-3-fluorobenzonitrile compound of formula (VI) [which can, for example, be prepared according to the process disclosed in J. Med. Chem., 40, 2064 (1997)] with a compound of formula (VII) to afford a compound of formula (III), followed by the reaction of said compound of formula (III) with a compound of formula (IV) to give the desired compound of formula (II).

In the definition of substituent $R^3$, the alkyl group having from 1 to 6 carbon atoms which is optionally substituted by at least fluorine atom is, for example, a methyl, fluoromethyl, difluoromethyl, trifluoromethyl, ethyl, 1-fluoroethyl, 2-fluoroethyl, 2,2-difluoroethyl, 2,2,2-trifluoroethyl, propyl, isopropyl, 3-fluoropropyl, butyl, isobutyl, sec-butyl, tert-butyl, 4-fluorobutyl, pentyl or hexyl group. Of these, alkyl groups having from 1 to 4 carbon atoms which are optionally substituted by from 1 to 3 fluorine atoms such as methyl, ethyl, propyl, butyl or 2,2,2-trifluoroethyl groups are preferred, unsubstituted alkyl groups having from 1 to 4 carbon atoms are more preferred and ethyl groups are most preferred.

In step B1 a compound of formula (III) is prepared by heating a 4-(halogeno-methyl)-3-fluorobenzonitrile compound of formula (VI) [which can, for example, be prepared according to the process disclosed in J. Med. Chem., 40, 2064 (1997)] with a compound of formula (VII) in the presence or absence of a solvent.

Examples of the compound of formula (IV) include 4-(chloromethyl)-3-fluorobenzonitrile and 4-(bromomethyl)-3-fluorobenzonitrile, of which 4-(bromomethyl)-3-fluorobenzonitrile is preferred.

Examples of the compound of formula (VII) include trialkyl phosphites, in which each alkyl group is the same or different and is a primary alkyl group having from 1 to 4 carbon atoms, such as trimethyl phosphite, triethyl phosphite, tripropyl phosphite or tributyl phosphite; and tris(fluoroalkyl) phosphites, in which each fluoroalkyl group is the same or different and is a primary alkyl group having from 1 to 4 carbon atoms which is substituted by at least one fluorine atom such as tris(2,2,2-trifluoroethyl) phosphite.

The preferred compounds of formula (VII) are the trialkyl phosphites, of which triethyl phosphite is most preferred.

The amount of the compound of formula (VII) employed is from 1 and 5 molar equivalents of amount of the compound of formula (VI) used, and is preferably from 1 to 1.5 molar equivalents of the compound of formula (VI).

The solvent employed in step B1 is not particularly limited provided that it has no adverse effect on the reaction and dissolves the starting materials to at least some extent. Suitable solvents are aprotic solvents, for example hydrocarbons such as hexane, cyclohexane, heptane, octane, nonane, decane or decalin; aromatic hydrocarbons which may optionally be substituted with at least one alkyl group or halogen atom such as benzene, toluene, xylene, mesitylene, ethylbenzene or chlorobenzene; halogenated hydrocarbons such as chloroform or dichloroethane; esters such as ethyl acetate or butyl acetate; ethers such as tetrahydrofuran, dimethoxyethane or dioxane; nitriles such as acetonitrile; and amide derivatives such as dimethylformamide; or mixture thereof. Preferably step B1 is conducted in the absence of a solvent.

The reaction temperature employed in step B1 depends upon various factors such as the nature of the starting materials and, if used, the solvent, but is typically between 80° C. and 170° C., and is preferably between 85° C. and 150° C.

The reaction time employed in step B1 mainly depends on the reaction temperature and the solvent, if one is used. It is usually from 0.5 to 24 hours, and is preferably from 1 to 3 hours.

After the reaction of step B1 is complete, volatile substances such as excess compound of formula (VII), by-products of the reaction and solvent are evaporated off to afford the desired product of formula (III), which can be used in the following step B2 without further purification.

The product of formula (III) can, if necessary, be purified using a conventional technique such as recrystallization, reprecipitation or chromatography.

In step B2 a compound of formula (II) or an acetal derivative thereof can be prepared by condensation of a compound of formula (III) with a compound of formula (IV) or with an acetal derivative thereof in the presence of base in a solvent, if necessary, followed by removal of the acetal protecting group if desired.

An acetal derivative of the compound of formula (IV) is a compound in which one of the two aldehyde groups of the compound of formula (IV) is protected with group of formula $CH(OR^1)(OR^2)$ wherein $R^1$ and $R^2$ are as defined above. Preferred acetal derivatives of the compound of formula (IV) include the dimethyl acetal and ethylene acetal derivatives, of which the dimethyl acetal derivative of the compound of formula (IV) is most preferred.

The compound of formula (IV) or an acetal derivative thereof can be prepared according to a procedure described in the literature [see, for example, Chem. Ber., 45, 1748 (1912); Tetrahedron Lett., 38, 1121 (1997); Justus Liebigs Ann. Chem., 638, 187 (1960); and J. Chem. Soc., Perkin Trans. 1, 1907 (1991)], or in a modified version of such literature procedures.

The amount of the compound of formula (IV) or acetal derivative thereof employed in Step B2 is usually from 0.5 to 1.5 molar equivalents of the amount of the compound of formula (III) used, and is preferably from 0.9 to 1.2 molar equivalents.

The solvent employed in this condensation reaction is not particularly limited provided that it has no adverse effect on the reaction and dissolves the starting materials to at least some extent. Suitable solvents include ethers such as tetrahydrofuran, dioxane or dimethoxyethane; hydrocarbons such as hexane, cyclohexane, benzene or toluene; sulfoxides such as dimethyl sulfoxide; or a mixture thereof. Ether solvents are preferred, of which tetrahydrofuran is particularly preferred.

The base used in step B2 is not particularly limited provided that it can abstract an active proton from the compound of formula (III). Suitable bases include organolithium compounds such as methyllithium, butyllithium or phenyllithium; metal hydrides such as lithium hydride, sodium hydride or potassium hydride; alkoxides such as sodium methoxide or potassium tert-butoxide; and sulfoxides metalated with an alkali metal such as dimesyl sodium. Of these, organolithium compounds are preferred, and butyllithium is particularly preferred.

The amount of base used is from 0.9 to 1.5 molar equivalents of the amount of the compound of formula (III), and is preferably from 1 to 1.1 molar equivalents.

The temperature of the condensation reaction mainly depends on the base employed. It is usually from −78° C. to ambient temperature, and is preferably from −20° C. to 10° C.

The reaction time for step B2 mainly depends on the reaction temperature and the solvent employed. It is usually from 30 minutes to 24 hours, and is preferably from 1 to 3 hours.

If an acetal protecting group is employed and the target compound is the free aldehyde of formula (II), an acid is added to the reaction mixture after the condensation reaction is complete, and the reaction mixture is then stirred to remove the acetal protecting group so as to afford the compound of formula (II).

The acid used for the removal of the acetal protecting group is not particularly limited provided that it does not affect any of the other substituents and it is one that is usually used in organic synthetic processes. Suitable examples of the acid which can be employed include inorganic acids such as hydrochloric acid, sulfuric acid or nitric acid; sulfonic acids such as methanesulfonic acid, benzenesulfonic acid, p-toluene-sulfonic acid, camphorsulfonic acid or trifluoromethanesulfonic acid; and carboxylic acids such as formic acid, acetic acid, trifluoroacetic acid, oxalic acid or citric acid. Of these, inorganic acids are preferred, and hydrochloric acid is particularly preferred.

The amount of acid used in the deprotection reaction is not particularly limited. Preferably, the amount of acid used is such that the resulting pH of the reaction mixture is from −1 to 3, preferably from 0 to 1.

The temperature used in the deprotection reaction is usually between −10° C. and 40° C., and is preferably between 0° C. and ambient temperature.

The reaction time of the deprotection reaction depends mainly on the pH of the reaction mixture and the reaction temperature. It is usually from 0.2 to 3 hours, and is preferably from 0.5 to 1.5 hours.

The reaction product of formula (II) or acetal derivative thereof can be isolated using a conventional technique, for example by partitioning the reaction mixture between an organic solvent and water, washing the organic layer with water, followed by evaporation of the solvent.

The product of formula (II) or acetal derivative thereof obtained above can be further purified by a conventional manner such as recrystallization, reprecipitation or chromatography.

Alternatively, the compound of formula (II) may be produced according to the method described in Japanese Patent Application (Kokai) Hei 8-333350 or by a modified version of said method.

The compound of formula (Ia), which is an isomer of the compound of formula (I), can be prepared according to Method A above using the compound of formula (Vb) below and the compound of formula (IIa) above as the starting materials.

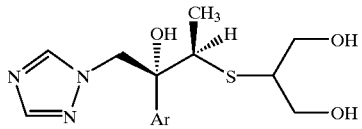

(Vb)

In this procedure a mixture of cis and trans isomers concerning the substituents at the 2- and 5-position on the 1,3-dioxane ring are obtained. The trans isomer of formula (Ia) can be isolated from the mixture of cis and trans isomers by chromatography or recrystallization. When water produced during the reaction in method A is removed under reduced pressure, the trans isomer is predominantly obtained.

The compound of formula (Vb) can be prepared according to the method described in Japanese Patent Application (Kokai) Hei 8-333350 or by a modified version of said method. The compound of formula (IIa) can be produced by the process of Method B using furmaraldehyde monodimethyl acetal as the starting material in Step B2.

Crystals of the compound of formula (Ib) or a salt thereof can be obtained from a supersaturated solution thereof. The supersaturated solution can be obtained in conventional manner such as through concentration of a solution of said compound of formula (Ib) or salt thereof, through the cooling of a solution of said compound of formula (Ib) or salt thereof or by adding a solvent in which said compound of formula (Ib) or salt thereof is sparingly soluble to a solution of said compound of formula (Ib) or salt thereof in which it is readily soluble. Precipitation of the crystals can take place spontaneously in the reaction vessel or it can be accelerated by the addition of a crystalline seed to the supersaturated solution of the compound of formula (Ib) or salt thereof, by mechanical stimulation such as through the use of ultrasonic waves or by scratching the inside of the reaction vessel.

A product of formula (Ib) isolated according to Method A or a crude reaction product containing the compound of formula (Ib) can be crystallized.

Where the supersaturated solution of the compound of formula (Ib) or salt thereof is to be obtained by concentration of a solution thereof, this can be conducted using a rotary evaporator or the like at atmospheric pressure or under reduced pressure with heating.

Where the supersaturated solution of the compound of formula (Ib) or salt thereof is to be obtained by cooling a solution thereof, the temperature used to cool the solution depends on the solvent employed and usually ranges from 0° to ambient temperature.

Where the supersaturated solution of the compound of formula (Ib) or salt thereof is to be obtained by adding a solvent in which said compound of formula (Ib) or salt thereof is sparingly soluble to a solution of said compound of formula (Ib) or salt thereof in which it is readily soluble, this can be conducted by first dissolving said compound of formula (Ib) or salt thereof in a solvent in which it is readily soluble and then adding the second solvent in which it is only slightly soluble and, if necessary, cooling the solution to afford crystals of the compound of formula (Ib).

Solvents in which the compound of formula (Ib) is readily soluble include acetates such as ethyl acetate; ketones such as acetone or 2-butanone; primary alcohols such as methanol, ethanol, propanol or butanol; cyclic ethers such as tetrahydrofuran; amides such as dimethylformamide or dimethylacetamide; sulfoxides such as dimethyl sulfoxide; nitriles such as acetonitrile; and halogenated hydrocarbons such as dichloromethane or chloroform. Of these, ethyl acetate, acetone or ethanol are preferred.

The solvents in which the compound of formula (Ib) is sparingly soluble depend on the nature of the solvent in which the compound of formula (Ib) is readily soluble. Suitable solvents include aliphatic hydrocarbons such as petroleum ether, pentane, hexane or heptane; non-cyclic ethers such as diethyl ether or diisopropyl ether; aromatic hydrocarbons such as benzene or toluene; secondary or tertiary alcohols such as 2-propanol or 2-methyl-2-propanol; and water. Of these, hexane, heptane, diisopropyl ether, 2-propanol or water are preferred.

The two preferred crystalline forms of the compound of formula (Ib) of the present invention are preferably produced through the addition of hexane to a solution of the compound of formula (Ib) in ethyl acetate or by dissolving the compound of formula (Ib) in a heated mixture of 2-propanol and ethyl acetate followed, if necessary, by cooling the solution.

The compounds of formula (I) and pharmaceutically acceptable salts and ester derivatives thereof exhibit excellent activity against many eumycetes. Examples of eumycetes include Candida species, Aspergillus species, Cryptococcus species, Mucor species, Histoplasma species, Blastomyces species, Coccidioides species, Paracoccidioides species, Trichophyton species, Epidermophyton species, Microsporum species, Malassezia species, Pseudallescheria species, Sporothrix species, Rhinosporidium species, Fonsecaea species, Wangiella species, Phialophora species, Exophiala species, Cladosporium species, Alternaria species, Aureobasidium species, Chaetomium species, Curvularia species, Drechslera species, Mycocentrospora species, Phoma species, Hendersonula species, Scytalidium species, Corynespora species, Leptospheria species, Madurella species, Neotestudina species, Scedosporium species, Pyrenochaeta species, Geotrichum species, Trichosporon species, Chrysosporium species, Coprinus species, Schizophyllum species, Pneumocystis species, Conidiobolus species, Basidiobolus species, Paecilomyces species, Penicillium species, Acremonium species, Fusarium species, Scopulariopsis species, Saccharomyces species, Cephalosporium species, Loboa species, Rhizopus species, Rhizomucor species and Absidia species.

As a result of this excellent antifungal activity, compounds of formula (I) and pharmaceutically acceptable salts and ester derivatives thereof can be used as a medicament, preferably as an antifungal agent.

The compound of formula (I) or a pharmaceutically acceptable salt or ester derivative thereof can be administered by itself or as a mixture of the compound of formula (I) or a pharmaceutically acceptable salt or ester derivative thereof with a pharmaceutically acceptable carrier(s). Compositions according to the present invention can be in unit dosage form such as tablets, capsules, granules, powders or syrups for oral administration or as injectable, topical, vaginal or percutaneous formulations or suppositories for parenteral administration or formulations suitable for inhalation (orally or intanasally).

The pharmaceutical compositions can be prepared in a known manner by using carriers such as excipients, binders, disintegrants, lubricants, stabilizers, corrigents, suspending agents, diluents and solvents.

Examples of suitable excipients includes sugar derivatives such as lactose, sucrose, glucose, mannitol or sorbitol; starch derivatives such as corn starch, potato starch, α-starch, dextrin or carboxymethylstarch; cellulose derivatives such as crystalline cellulose, low-substituted hydroxypropylcellulose, hydroxypropyl-methylcellulose, carboxymethylcellulose or internally-cross-linked sodium carboxymethylcellulose; gum arabic; dextran; pullulan; silicate derivatives such as light silicic acid anhydride, synthetic aluminum silicate or magnesium aluminate metasilicate; phosphate derivatives such as calcium phosphate; carbonate derivatives such as calcium carbonate; sulfate derivatives such as calcium sulfate; glycols; and colloidal silica.

Examples of suitable binders include starch derivatives and cellulose derivatives such as those described above, gelatin, polyvinylpyrrolidone and Macrogol.

Examples of suitable disintegrants include starch derivatives and cellulose derivatives such as those described above, a chemically modified starch or cellulose derivative such as sodium cross-carmelose, sodium carboxymethylstarch and cross-linked polyvinylpyrrolidone.

Examples of suitable lubricants include talc; stearic acid; metal stearate derivatives such as calcium stearate or magnesium stearate; waxes such as bee's wax or spermaceti; glycols; carboxylic acids such as fumaric acid; sulfates such as calcium sulfate; leucine; silicic acid derivatives such as silicic acid anhydride or silicic acid hydrate; and starch derivatives such as those described above for excipients.

Examples of stabilizers include para-hydroxybenzoic acid ester derivatives such as methylparaben or propylparaben; alcohols such as chlorobutanol, benzyl alcohol or phenethyl alcohol; benzalkonium chloride; phenol derivatives such as phenol or cresol; thimerosal; acetic anhydride; sorbic acid; boric acid; adipic acid; sodium carboxylates such as sodium benzoate; lauryl sulfates such as sodium lauryl sulfate or magnesium lauryl sulfate; antioxidants such as retinol, tocoferol or sodium ascorbate; and synthetic hydrotalcite.

Examples of corrigents includes sweeteners, souring agents and flavoring agents commonly used for the purpose.

Examples of suspending agents include polysorbate 80 and sodium carboxymethylcellulose.

Examples of suitable solvents for the preparation of formulations for parenteral administration include water, ethanol, glycerin, physiological saline, glucose solution, water containing α-, β- or γ-cyclodextrin having 2 to 11 hydroxypropyl groups per molecule of cyclodextrin, propylene glycol, polyethylene glycol 200 and polyethylene glycol 400.

The dose of the compound of formula (I) or pharmaceutically acceptable salt or ester derivative thereof will vary depending on a variety of factors such as the age and symptoms of the human patient and the route of administration. A suitable dosage level for oral administration is from 1 mg (preferably 5 mg) per day as a lower limit to 2000 mg (preferably 1000 mg) per day as an upper limit for an adult. A suitable dosage level for intravenous administration is from 0.1 mg (preferably 0.5 mg) per day as a lower limit to 600 mg (preferably 500 mg) per day as an upper limit for an adult. The compound of formula (I) or a pharmaceutically acceptable salt or ester derivative thereof can be administered either as a single unit dosage or, if desired, the dosage may be divided into convenient sub-units administered from one to six times throughout the day depending on the symptoms of the patient.

The following examples, reference examples, test examples and formulation examples are intended to further illustrate the present invention and are not intended to limit the scope of the invention in any way.

EXAMPLE 1

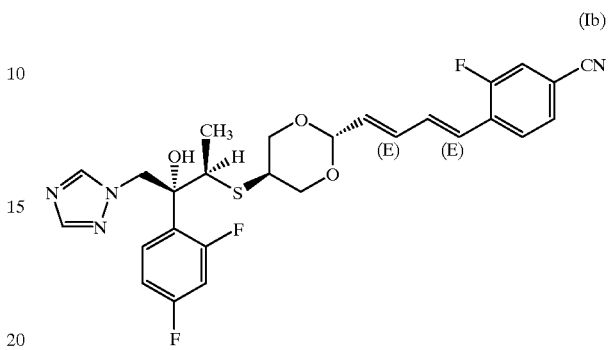

(Ib)

1(i) Diethyl 4-cyano-2-fluorobenzylphosphonate

A mixture of 1.5 g (7.0 mmol) of 4-(bromomethyl)-3-fluorobenzonitrile [ref. J.Med.Chem., 40, 2064 (1997)] and 1.4 g (8.4 mmol) of triethyl phosphite was heated at 150° C. for 2 hours. At the end of this time, the reaction mixture was concentrated under reduced pressure. Volatile materials in the residue thus obtained were removed by heating said residue at 100° C. in vacuo for 1 hour to afford 1.97 g (quantitative yield) of the title compound as an oil which solidified in the freezer. This oily product was used in the next step without further purification.

$^1$H-Nuclear magnetic resonance spectrum (270 MHz, CDCl$_3$) δ ppm: 1.27 (6H, triplet, J=7.1 Hz); 3.24 (2H, doublet, J=22.3 Hz); 4.00–4.05 (4H, multiplet); 7.37 (1H, doublet, J=9.2 Hz); 7.43 (1H, doublet, J=7.9 Hz); 7.51 (1H, triplet of doublets, J$_t$=9.2 Hz, J$_d$=2.6 Hz).

IR spectrum ν$_{max}$ (CHCl$_3$) cm$^{-1}$: 2237, 1262, 1054, 1029.

Mass spectrum m/z (EI): 271(M$^+$), 139, 109(100%), 93.

1(ii) 3-Fluoro-4-[(1E,3E)-5-oxo-1,3-pentadienyl] benzonitrile 0.5 ml (0.77 mmol) of a 1.53 N hexane solution of butyllithium were added dropwise to a solution of 209 mg (0.77 mmol) of diethyl 4-cyano-2-fluorobenzyl-phosphonate [which was obtained in Step 1(i) above] in 4 ml of anhydrous tetrahydrofuran at −78° C. with stirring. The mixture was stirred at −78° C. for 30 minutes. At the end of this time, a solution of 100 mg (0.77 mmol) of commercially available fumaraldeyde mono-dimethylacetal in 2 ml of anhydrous tetrahydrofuran was added to the mixture, and the resulting mixture was stirred at −78° C. for 2 hours. The cooling bath was then removed and the mixture was stirred in an ice bath for a further 15 minutes. 3.9 ml (0.39 mmol) of 0.1 N hydrochloric acid were added to the reaction mixture and the mixture was then stirred for 30 minutes in the ice bath and then for 1 hour at ambient temperature. At the end of this time, a saturated aqueous sodium hydrogen carbonate solution was added to the mixture in an ice bath. The resulting mixture was partitioned between ethyl acetate and water, the organic layer was washed with water and with aqueous sodium chloride solution, dried over anhydrous magnesium sulfate and then concentrated under reduced pressure. The crystalline residue thus obtained was recrystallized from a mixture of ethyl acetate and hexane to afford 127 mg (yield 87%) of the title compound as pale yellow crystals.

mp: 174–177° C.

$^1$H-Nuclear magnetic resonance spectrum (270 MHz, CDCl$_3$) δ ppm: 6.36 (1H, doublet of doublets, J=15, 8 Hz); 7.14 (1H, doublet-like, J=3 Hz); 7.16 (1H, doublet, J=8 Hz); 7.28 (1H, double doublet of doublets, J=15, 8, 3 Hz); 7.40 (1H, doublet of doublets, J=10, 1 Hz); 7.47 (1H, doublet of doublets, J=8, 1 Hz); 7.67 (1H, triplet, J=8 Hz), 9.68 (1H, doublet, J=8 Hz).

IR spectrum $v_{max}$ (KBr) cm$^{-1}$: 2230, 1681, 1672, 1621, 1421, 1159, 1124.

Mass spectrum m/z (EI): 201(M$^+$), 172(100%), 158, 145.

Anal. calculated for $C_{12}H_8FNO$: C, 71.64; H, 4.01; N, 6.96. Found: C, 71.84; H, 4.27; N, 6.83.

1(iii) (2R,3R)-3-[[trans-2-[(1E,3E)-4-(4-Cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol A mixture of 4.63 g (23.0 mmol) of 3-fluoro-4-[(1E,3E)-5-oxo-1,3-pentadienyl]benzonitrile [produced as described in Step 1(ii) above], 8.73 g (24.3 mmol) of (2R,3R)-2-(2,4-difluorophenyl)-3-[[1-(hydroxymethyl)-2-hydroxyethyl]thio]-1-(1H-1,2,4-triazol-1-yl)-2-butanol [produced as described in Japanese Patent Application (Kokai) Hei 8-333350)], 5.07 g (26.7 mmol) of p-toluenesulfonic acid monohydrate and 200 ml of anhydrous tetrahydrofuran was allowed to stand at ambient temperature for 30 minutes. At the end of this time, the reaction mixture was concentrated using a rotary evaporator and dried in vacuo. The resulting residue was dissolved in 150 ml of anhydrous tetrahydrofuran and the resulting mixture was then evaporated to dryness in vacuo using a rotary evaporator. This procedure was repeated twice more. A solution of the resulting residue in 150 ml of anhydrous tetrahydrofuran was poured into a saturated aqueous sodium hydrogen carbonate solution with stirring. The product was then extracted with ethyl acetate and the organic layer was washed with aqueous sodium chloride solution, dried over anhydrous magnesium sulfate and then concentrated under reduced pressure. The residual oil was purified by chromatography on a silica gel (500 g) column using a 2:1 mixture of ethyl acetate and hexane as the eluant to give 9.35 g (yield 74%) of the title compound as a yellow amorphous solid.

$^1$H-Nuclear magnetic resonance spectrum (400 MHz, CDCl$_3$) δ ppm: 1.19 (3H, doublet, J=7 Hz); 3.33 (1H, quartet, J=7 Hz); 3.40 (1H, triplet of triplets, J=11, 5 Hz); 3.62 (1H, triplet, J=11 Hz); 3.64 (1H, triplet, J=11 Hz); 4.30 (1H, double doublet of doublets, J=11, 5, 2 Hz); 4.43 (1H, double doublet of doublets, J=11, 5, 2 Hz); 4.83 (1H, doublet, J=14 Hz); 5.01 (1H, s); 5.03 (1H, doublet, J=14 Hz); 5.07 (1H, doublet, J=4 Hz); 5.90 (1H, doublet of doublets, J=15, 4 Hz); 6.62 (1H, doublet of doublets, J=15, 11 Hz); 6.7–6.8 (2H, multiplet); 6.73 (1H, doublet, J=16 Hz); 6.95 (1H, doublet of doublets, J=16, 11 Hz); 7.3–7.4 (1H, multiplet); 7.34 (1H, doublet, J=9 Hz); 7.40 (1H, doublet, J=8 Hz); 7.58 (1H, triplet, J=8 Hz); 7.79 (2H, singlet).

IR spectrum $v_{max}$ (KBr) cm$^{-1}$: 2232, 1616, 1499, 1418, 1140.

Mass spectrum m/z (FAB): 543(M$^+$+1).

Specific rotation: $[α]_D^{25}$ –76.6° (c=1.00, CHCl$_3$).

EXAMPLE 2

Crystalline (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol, prepared as described in Example 1, was dissolved in a hot 9:1 mixture of 2-propanol and ethyl acetate. The resulting solution was then irradiated with ultrasonic waves in an ultrasonic bath to afford a powdery form of the title compound, which was collected by filtration.

Melting Point: 111–112° C.

IR spectrum $v_{max}$ (KBr) cm$^{-1}$: 2232, 1616, 1499, 1419, 1141.

A powder X ray diffraction pattern of the crystalline product, illustrated in FIG. 1, was obtained by irradiation of the crystalline product using the copper K$_α$ ray. The vertical axis of the powder X ray diffraction pattern indicates the diffraction intensity in units of counts/second (cps). The horizontal axis indicates the diffraction angle as the value 2θ. The spacing of the lattice planes d can be calculated using the equation 2d sin θ=nλ in which n is 1.

EXAMPLE 3

Crystalline (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol, obtained as described in Example 1, was dissolved in ethyl acetate and then the same amount of hexane as that of the ethyl acetate was added to the solution to precipitate crystals of the title compound.

Melting Point: 127–128° C.

IR spectrum $v_{max}$ (KBr) cm$^{-1}$: 2232, 1616, 1499, 1419, 1140.

Figure 2:
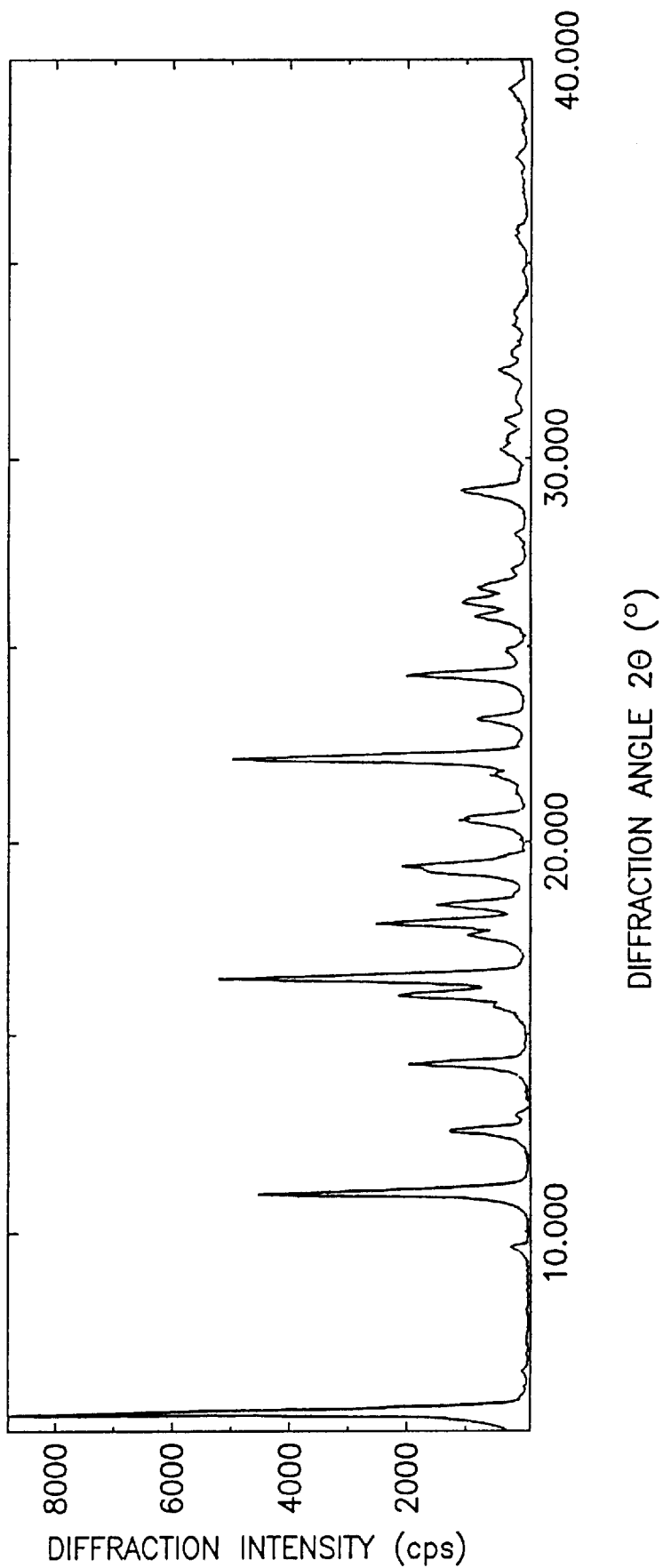
FIG. 2 shows the X-ray diffraction pattern of a second crystalline form of (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol, by the powder method using the copper $K_\alpha$-ray, $\lambda=1.54$ Å. The vertical axis of the powder X-ray diffraction pattern indicates diffraction intensity in units of counts/second (cps), while the horizontal axis indicates the diffraction angle as the value 2θ.

A powder X ray diffraction pattern of the crystalline product, illustrated in FIG. 2, was obtained by irradiation of the crystalline product using the copper K$_α$ray. The vertical axis of the powder X ray diffraction pattern indicates the diffraction intensity in units of counts/second (cps). The horizontal axis indicates the diffraction angle as the value 2θ. The spacing of the lattice planes d can be calculated using the equation 2d sin θ=nλ in which n is 1.

EXAMPLE 4

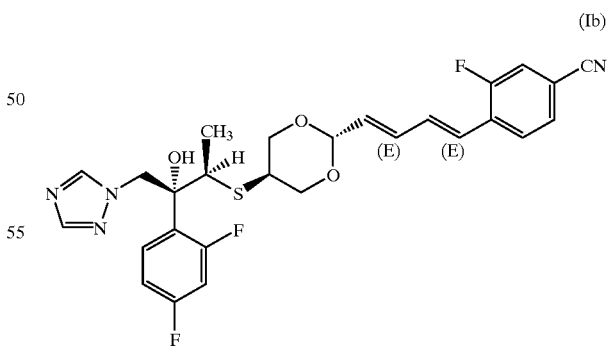

(Ib)

791 mg (4.16 mmol) of p-toluenesulfonic acid monohydrate were added to a solution of 760 mg (3.77 mmol) of 3-fluoro-4-[(1E,3E)-5-oxo-1,3-pentadienyl]-benzonitrile [obtained as described in Example 1(ii) above] and 1.36 g (3.77 mmol) of (2R,3R)-2-(2,4-difluorophenyl)-3-[[1-(hydroxymethyl)-2-hydroxyethyl]thio]-1-(1H-1,2,4-triazol- 1-yl)-2-butanol [prepared as described in Japanese Patent Application (Kokai) Hei 8-333350] in 13 ml of dichloromethane. The resulting mixture was concentrated using a rotary evaporator. 13 ml of dichloromethane and 13 g of 4A molecular sieves were added to the resulting residue and the mixture was then stirred at ambient temperature overnight. At the end of this time, an aqueous sodium hydrogen carbonate solution was added to the reaction mixture. The molecular sieves were removed by filtration and the filtrate was partitioned between ethyl acetate and water. The organic layer was dried and concentrated under reduced pressure. The resulting oily residue was purified by chromatography on a silica gel (20 g) column using a 1:1 mxiture of ethyl acetate and hexane as the eluant to afford 1.42 g (yield 69%) of the title compound as an amorphous solid. The spectral data were identical to those of the title compound of Example 1.

EXAMPLE 5

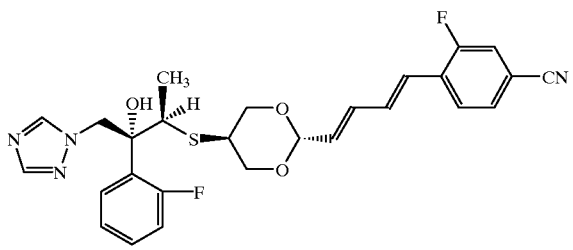

5(i) (2R,3R)-2-(2-Fluorophenyl)-3-[(trans-2-phenyl-1,3-dioxan-5-yl)thio]-1-(1H-1,2,4-triazol-1-yl)-2-butanol 0.12 ml (0.59 mmol) of a 4.9 M methanolic solution of sodium methoxide were added to a solution of 0.93 g (4.0 mmol) of (2R,3S)-2-(2-fluorophenyl)-3-methyl-2-[(1H-1,2,4-triazol-1-yl)methyl]oxirane [prepared as described in Chem. Pharm. Bull., 43, 441–449 (1995)] and 1.14 g (4.8 mmol) of trans-5-(acetylthio)-2-phenyl-1,3-dioxane [prepared as described in Japanese Patent Application (Kokai) Hei 8-333350] in 15 ml of ethanol. The resulting mixture was stirred at 87° C. for 13 hours. After cooling, the reaction mixture was partitioned between ethyl acetate and an aqueous ammonium chloride solution. The organic solution was washed with saturated aqueous sodium chloride solution and then concentrated under reduced pressure. The resulting oily residue was purified by chromatography on a silica gel (75 g) column using a 3:2 mixture of ethyl acetate and hexane as the eluant to afford 0.68 g (yield 40%) of the title compound as a non-crystalline solid.

$^1$H-Nuclear magnetic resonance spectrum (400 MHz, CDCl$_3$) δ ppm: 1.21 (3H, doublet, J=7 Hz); 3.42 (1H, quartet, J=7 Hz); 3.49 (1H, triplet of triplets, J=11, 5 Hz); 3.75 (2H, triplet, J=11 Hz); 3.72 (2H, triplet, J=11 Hz); 4.41 (1H, double doublet of doublets, J=11, 5, 2 Hz); 4.52 (1H, double doublet of doublets, J=11, 5, 2 Hz); 4.89 (1H, doublet, J=14 Hz); 4.92 (1H, doublet, J=1 Hz); 5.07 (1H, doublet, J=14 Hz); 5.49 (1H, singlet); 6.94–7.03 (2H, multiplet); 7.17–7.23 (1H, multiplet); 7.33–7.41 (3H, multiplet); 7.49 (2H, doublet of doublets, J=7, 2 Hz); 7.75 (1H, singlet); 7.77 (1H, singlet).

IR spectrum ν$_{max}$ (CHCl$_3$) cm$^{-1}$: 3131, 1732, 1376, 1140.

Mass spectrum m/z (FAB): 430 (M$^+$+1).

5(ii) (2R,3R)-2-(2-Fluorophenyl)-3-[[1-hydroxymethyl)-2-hydroxyethyl]thio]-1-(1H-1,2,4-triazol-1-yl)-2-butanol 110 ml (110 mmol) of 1 N hydrochloric acid were added to a solution of 13 g (30.3 mmol) of (2R,3R)-2-(2-fluorophenyl)-3-[(trans-2-phenyl-1,3-dioxan-5-yl)thio]-1-(1H-1,2,4-triazol-1-yl)-2-butanol [prepared as described in Step 5(i) above] in 80 ml of toluene. The resulting mixture was heated at 50° C. for 2.5 hours. At the end of this time, the water layer was separated and the oily layer was extracted twice with dilute hydrochloric acid and then with an aqueous sodium chloride solution. The aqueous layers were combined and sodium hydrogen carbonate was carefully added thereto in small portions until bubbles of carbon dioxide were no longer detected. The resulting mixture was extracted with ethyl acetate and the extract was then concentrated under reduced pressure to afford a solid residue. This residue was collected by filtration and then washed with a small amount of ethyl acetate to afford 5.57 g (yield 55%) of the title compound as a pale brown solid.

Melting Point: 121–123° C.

$^1$H-Nuclear magnetic resonance spectrum (400 MHz, CDCl$_3$) δ ppm: 1.21 (3H, doublet, J=7 Hz); 2.47 (1H, triplet, J=6 Hz); 2.78 (1H, triplet, J=6 Hz); 3.24 (1H, quintet, J=6 Hz); 3.50 (1H, quartet, J=7 Hz); 3.7–4.0 (4H, multiplet); 4.92 (1H, doublet, J=14 Hz); 5.14 (1H, doublet, J=14 Hz); 5.16 (1H, singlet); 6.97 (1H, double doublet of doublets, J=12, 8, 1 Hz); 7.02 (1H, triplet of doublets, J=8, 1 Hz); 7.22 (1H, triple doublet of doublets, J=8, 5, 2 Hz); 7.39 (1H, triplet of doublets, J=8, 2 Hz); 7.765 (1H, singlet); 7.770 (1H, singlet).

IR spectrum ν$_{max}$ (KBr)cm$^{-1}$: 1513, 1485, 1451, 1275, 1209, 1136, 1072, 1054.

Mass spectrum m/z (FAB): 342 (M$^+$+1).

Specific rotation: [α]$_D^{25}$ −78.2° (c=1.16, CHCl$_3$).

Anal. calculated for C$_{15}$H$_{20}$F$_2$N$_4$O$_3$S: C, 52.77; H, 5.91; N, 12.31. Found: C, 52.74; H, 5.95; N, 12.24.

5(iii) (2R,3R)-3-[[trans-2-[(1E,3E)-4-(4-Cyano-2-fluorolphenyl)-1,3-butadien-1-yl]-1,3-dioxan-5-yl]thio]-2-(2-fluorophenyl)-1-(1H-1,2,4-triazol-1-yl)-2-butanol The crude title compound was obtained as an oil in a similar manner to that described in Example 1(iii) above using 510.7 mg (1.50 mmol) of (2R,3R)-2-(2-fluorophenyl)-3-[[1-(hydroxymethyl)-2-hydroxyethyl]thio]-2-butanol [prepared as described in step 5(ii) above], 300 mg (1.5 mmol) of 3-fluoro-4-[(1E,3E)-5-oxo-1,3-pentadienyl] benzonitrile [prepared as described in Example 1(ii) above] and 283.1 mg (1.64 mmol) of p-toluenesulfonic acid monohydrate. The oil was purified by chromatography on a column silica gel (50 g) using a 1:1 mixture of ethyl acetate and hexane as the eluant to give 431 mg (yield 55%) of the title compound as a colorless non-crystalline solid.

$^1$H-Nuclear magnetic resonance spectrum (400 MHz, CDCl$_3$) δ ppm: 1.19 (3H, doublet, J=7 Hz); 3.39 (1H, quartet, J=7 Hz); 3.38–3.45 (1H, multiplet); 3.62 (1H, triplet, J=11 Hz); 3.65 (1H, triplet, J=11 Hz); 4.31 (1H, double doublet of doublets, J=11, 5, 2 Hz); 4.44 (1H, double doublet of doublets, J=11, 5, 2 Hz); 4.87 (1H, doublet, J=14 Hz); 4.92 (1H, singlet); 5.04 (1H, doublet, J=14 Hz); 5.07 (1H, doublet, J=4 Hz); 5.90 (1H, doublet of doublets, J=15, 4 Hz); 6.62 (1H, doublet of doublets, J=15, 11 Hz); 6.75 (1H, doublet, J=15 Hz); 6.98 (1H, doublet of doublets, J=15, 11 Hz); 6.92–7.02 (2H, multiplet); 7.18–7.23 (1H, multiplet); 7.32–7.36 (2H, multiplet); 7.41 (1H, doublet of doublets. J=8, 1 Hz); 7.58 (1H, triplet, J=8 Hz); 7.75 (1H, singlet); 7.77 (1H, singlet).

IR spectrum ν$_{max}$ (KBr) cm$^{-1}$: 3426, 2852, 2231, 1141.

Mass spectrum m/z (FAB): 525 (M$^+$+1).

EXAMPLE 6

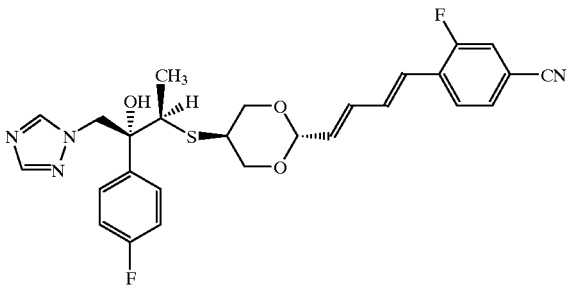

6(i) cis-5-(Acetylthio)-2-phenyl-1,3-dioxane

A mixture of 30 g (90 mmol) of trans-2-phenyl-5-(p-toluenesulfonyloxy)-1,3-dioxane (prepared as described in Tetrahedron, 48, 5941–5950), 15.3 g (134 mmol) of potassium thioacetate, 240 ml of toluene and 60 ml of N,N-dimethylacetamide was stirred at 100° C. for 3 hours and then at 110–120° C. for 7 hours. After cooling, the reaction mixture was partitioned between toluene and water. The organic layer was then washed with water, dried over anhydrous magnesium sulfate and concentrated. The resulting oily residue was purified by chromatography on a silica gel (200 g) column using a 1:4 mixture of ethyl acetate and hexane as the eluant to afford the crude title compound as a solid. This solid was recrystallized from a mixture of ethyl acetate and hexane to afford 10 g (yield 47%) of the title compound as brown needle-like crystals.

Melting Point: 94–95° C.

$^1$H-Nuclear magnetic resonance spectrum (270 MHz, CDCl$_3$) δ ppm: 2.39 (3H, singlet); 3.71 (1H, broad singlet); 4.19 (2H, broad doublet, J=12 Hz); 4.38 (2H, broad doublet, J=12 Hz); 5.55 (1H, singlet); 7.30–7.42 (3H, multiplet); 7.42–7.55 (2H, multiplet).

IR spectrum $v_{max}$ (KBr) cm$^{-1}$: 1676, 1402, 1130.

Mass spectrum m/z (EI): 238 (M$^+$), 237, 178, 107, 105, 43 (100%).

6(ii) (2R,3R)-2-(4-Fluorophenyl)-3-[(cis-2-phenyl-1,3-dioxan-5-yl)thio]-1-(1H-1,2,4-triazol-1-yl)-2-butanol 1 ml (0.59 mmol) of a 4.8 M methanolic solution of sodium methoxide was added to a solution of 2.33 g (10 mmol) of (2R,3S)-2-(4-fluorophenyl)-3-methyl-2-[(1H-1,2,4-triazol-1-yl)methyl]oxirane [prepared as described in Chem. Pharm. Bull., 43, 441–449 (1995)] and 2.38 g (10 mmol) of cis-5-(acetylthio)-2-phenyl-1,3-dioxane [prepared as descripted in Step 6(i) above] in 40 ml of ethanol. The resulting mixture was stirred at 80° C. for 5 hours. After cooling, the reaction mixture was partitioned between ethyl acetate and water. The organic layer was separated and washed with saturated aqueous sodium chloride solution, dried over anhydrous magnesium sulfate and then concentrated under reduced pressure. The residue was purified by chromatography on a silica gel (50 g) column using a 2:1 mixture of ethyl acetate and hexane as the eluant to afford 3.1 g (yield 72%) of the title compound as a brown foamy solid.

$^1$H-Nuclear magnetic resonance spectrum (270 MHz, CDCl$_3$) δ ppm: 1.29 (3H, doublet, J=7 Hz); 2.97 (1H, multiplet); 3.50 (1H, quartet, J=7 Hz); 4.26 (1H, doublet-like, J=12 Hz); 4.36 (1H, doublet of doublets, J=12, 3 Hz); 4.36 (1H, doublet of doublets, J=12, 2 Hz); 4.42 (1H, doublet of doublets, J=12, 3 Hz); 4.56 (1H, singlet); 4.57 (1H, doublet, J=14 Hz); 5.10 (1H, doublet, J=14 Hz); 5.61 (1H, singlet); 6.89 (2H, triplet, J=9 Hz); 7.16 (1H, doublet of doublets, J=9, 5 Hz); 7.3–7.5 (3H, multiplet); 7.4–7.6 (2H, multiplet); 7.69 (1H, singlet); 7.80 (1H, singlet).

IR spectrum $v_{max}$ (CHCl$_3$) cm$^{-1}$: 1732, 1605, 1509, 1278, 1135.

Mass spectrum m/z (FAB): 430 (M$^+$+1).

Specific rotation: $[\alpha]_D^{25}$ −59.8° (c=1.29, CHCl$_3$).

6(iii) (2R,3R)-2-(4-fluorophenyl)-3-[[1-(hydroxymethyl)-2-hydroxyethyl]thio]-(1-(1H-1,2,4-triazol-1-yl)-2-butanol 1 ml (12 mmol) of 12 N hydrochloric acid were added to a solution of 3.1 g (7.2 mmol) of (2R,3R)-2-(4-fluorophenyl)-3-[(cis-2-phenyl-1,3-dioxan-5-yl)thio]-1-(1H-1,2,4-triazol-1-yl)-2-butanol [prepared as described in Step 6(ii) above] in 39 ml of methanol. The resulting mixture was stirred at ambient temperature for 16 hours. At the end of this time, an aqueous sodium hydrogen carbonate solution was carefully added to the reaction mixture until the solution became weakly alkaline. Most of the methanol was evaporated from the mixture under reduced pressure. The resulting residue was then partitioned between ethyl acetate and aqueous sodium chloride solution. The organic layer was dried over anhydrous magnesium sulfate and then concentrated under reduced pressure. The resulting residue was purified by chromatography on a silica gel (30 g) column using a 1:9 mixture of methanol and ethyl acetate as the eluant to afford 2.15 g (yield 87%) of the title compound as a hygroscopic pale brown foamy solid.

$^1$H-Nuclear magnetic resonance spectrum (270 MHz, CDCl$_3$) δ ppm: 1.26 (3H, doublet, J=7 Hz); 2.6–2.8 (2H, broad); 3.16 (1H, quintet, J=6 Hz); 3.27 (1H, quartet, J=7 Hz); 3.6–4.0 (4H, multiplet); 4.66 (1H, doublet, J=14 Hz); 4.92 (1H, singlet); 4.94 (1H, doublet, J=14 Hz); 6.99 (2H, triplet, J=9 Hz); 7.25 (2H, doublet of doublets, J=9, 5 Hz); 7.75 (1H, singlet); 7.84 (1H, singlet).

IR spectrum $v_{max}$ (CHCl$_3$) cm$^{-1}$: 1605, 1510, 1277.

Mass spectrum m/z (FAB): 342 (M$^+$+1).

Specific rotation: $[\alpha]_D^{25}$ −26.9° (c=1.55, CHCl$_3$).

6(iv) (2R,3R)-3-[[trans-2-[(1E,3E)-4-(4-Cyano-2-fluorophenyl)-1,3-butadien-1-yl]-1,3-dioxan-5-yl]thio]-2-(4-fluorophenyl)-1-(1H-1,2,4-triazol-1-yl)-2-butanol The crude title compound was obtained as an oil in a similar manner to that described in Example 1(iii) above using 510.7 mg (1.50 mmol) of (2R,3R)-2-(4-fluorophenyl)-3-[[1-(hydroxymethyl)-2-hydroxyethyl]thio]-2-butanol [prepared as described in Step 6(iii) above], 301 mg (1.5 mmol) of 3-fluoro-4-[(1E,3E)-5-oxo-1,3-pentadienyl]benzonitrile [prepared as described in Example 1 (ii) above] and 283 mg (1.64 mmol) of p-toluenesulfonic acid monohydrate. The oil was purified by chromatography on a silica gel column using a 1:1 mixture of ethyl acetate and hexane as the eluant to give 214 mg (yield 27%) of the title compound as a colorless non-crystalline solid.

$^1$H-Nuclear magnetic resonance spectrum (400 MHz, CDCl$_3$) δ ppm: 1.21 (3H, doublet, J=7 Hz); 3.13 (1H, quartet, J=7 Hz); 3.33 (1H, triplet of triplets, J=11, 5 Hz); 3.58 (1H, triplet, J=11 Hz); 3.60 (1H, triplet, J=11 Hz); 4.26 (1H, double doublet of doublets, J=11, 5, 2 Hz); 4.37 (1H, double doublet of doublets, J=11, 5, 2 Hz); 4.52 (1H, doublet, J=14 Hz); 4.60 (1H, singlet); 4.98 (1H, doublet, J=14 Hz); 5.04 (1H, doublet, J=4 Hz); 5.89 (1H, doublet of doublets, J=15, 4 Hz); 6.60 (1H, doublet of doublets, J=15, 10 Hz); 6.74 (1H, doublet, J=16 Hz); 6.94 (1H, doublet of doublets, J=16, 10 Hz); 6.95–6.99 (2H, multiplet); 7.21–7.24 (2H, multiplet); 7.34 (1H, doublet of doublets, J=10, 1 Hz); 7.40 (1H, doublet of doublets, J=8, 1 Hz); 7.58 (1H, triplet, J=8 Hz); 7.71 (1H, singlet); 7.83 (1H, singlet).

IR spectrum $v_{max}$ (KBr) cm$^{-1}$: 3428, 2231, 1509, 1140.

Mass spectrum m/z (FAB): 525 (M$^+$+1).

EXAMPLE 7

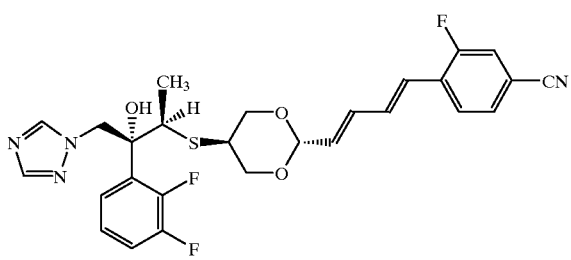

7(i) (2R)-2',3'-Difluoro-2-(3,4,5,6-tetrahydro-2H-pyran-2-yloxy)propiophenone

A mixture of 0.5 g (2.6 mmol) of 1-bromo-2,3-difluorobenzene. 0.681 g (28 mmol) of metallic magnesium and 40 ml of tetrahydrofuran was heated to initiate generation of a Grignard reagent. When the reaction had started, the mixture was cooled to 0° C. A solution of 4.5 g (23 mmol) of 1-bromo-2,3-difluorobenzene in 30 ml of tetrahydrofuran was added to the mixture over a period of 0.5 hours. At the end of this time, the mixture was then stirred at ambient temperature for 1.5 hours. The mixture was cooled to −30° C. and a solution of 4.87 g (20 mmol) of 4-[(2R)-2-(3,4,5,6-tetrahydro-2H-pyran-2-yloxy)propionyl] morpholine [prepared as described in Chem. Pharm. Bull., 41, 1035–1042 (1993)] in 30 ml of tetrahydrofuran was added dropwise to the mixture over a period of 20 minutes. The resulting mixture was then stirred at ambient temperature for 2 hours, after which the reaction was stopped by the addition of a saturated aqueous ammonium chloride solution. The reaction product was extracted with ethyl acetate and the organic layer was washed with aqueous sodium chloride solution and then concentrated under reduced pressure. The oily residue thus obtained was purified by chromatography on a silica gel (75 g) column using a 1:9 mixture of ethyl acetate and hexane as the eluant to afford 4.80 g (yield 89%) as a colorless oil.

$^1$H-Nuclear magnetic resonance spectrum (400 MHz, CDCl$_3$) δ ppm: 1.44 [(3/2)H, doublet of doublets. J=7, 1 Hz]; 1.49 [(3/2)H, doublet of doublets, J=7, 1 Hz]; 1.49–1.90 (6H, multiplet); 3.33–3.38 [(1/2)H, multiplet]; 3.50–3.55 [(1/2)H, multiplet]; 3.68–3.74 [(1/2)H, multiple]; 3.87–3.93 [(1/2)H, multiplet]; 4.66 [(1/2)H, triplet, J=4 Hz]; 4.75 [(1/2)H, triplet, J=4 Hz]; 4.85 [(1/2)H, quartet of doublets, J=7, 2 Hz]; 5.10 [(1/2)H, quartet of doublets, J=7, 2 Hz]; 7.14–7.21 (1H, multiplet); 7.30–7.39 (1H, multiplet); 7.54–7.58 (1H, multiplet).

IR spectrum $v_{max}$ (CHCl$_3$) cm$^{-1}$: 1700, 1481, 1273.

Mass spectrum m/z (FAB): 271 (M$^+$+1).

7(ii) (2R,3R)-2-(2,3-Difluorophenyl)-1,2,3-butanetriol (Dimethylisopropoxysilyl)methylmagnesium chloride was prepared from a solution of 5.74 g (34.4 mmol) of chloromethyldimethylisopropoxysilane in 40 ml tetrahydrofuran and 0.84 g (34.4 mmol) of metallic magnesium. A solution of 4.65 g (17.2 mmol) of (2R)-2',3'-difluoro-2-(3,4,5,6-tetrahydro-2H-pyran-2-yloxy)propiophenone [prepared as described in Step 7(i) above] in 20 ml of tetrahydrofuran was added to the solution of the Grignard reagent at 0° C. with stirring. The resulting mixture was stirred at ambient temperature for 30 minutes, after which the reaction was stopped by the addition of a saturated aqueous ammonium chloride solution to the reaction mixture. The reaction product was extracted with ethyl acetate. The organic layer was washed with aqueous sodium chloride solution and concentrated to afford 8.1 g of crude (2S,3R)-2-(2,3-difluorophenyl)-1-(isopropoxydimethylsilyl)-3-(3,4,5,6-tetrahydro-2H-pyran-2-yloxy)-2-butanol as an oil.

1.4 g (17 mmol) of sodium hydrogen carbonate and 16 ml of a 31% aqueous hydrogen peroxide solution were added to a solution of the crude oil in a mixture of 40 ml of methanol and 40 ml of tetrahydrofuran. The resulting mixture was stirred at 80° C. for 40 minutes. After cooling the reaction mixture, the reaction product was extracted with ethyl acetate. The organic layer was washed with aqueous sodium chloride solution and concentrated to afford 10 g of crude (2R,3R)-2-(2,3-difluorophenyl)-3-(3,4,5,6-tetrahydro-2H-pyran-2-yloxy)-1,2-butanediol as an oil.

0.20 g (1.05 mmol) of p-toluenesulfonic acid monohydrate were added to a solution of the oil in 40 ml of methanol. The resulting mixture was stirred at ambient temperature for 1 hour. At the end of this time, the reaction mixture was concentrated under reduced pressure. The resulting residue was purified by chromatography on a silica gel (125 g) column using a 1:1 mixture of ethyl acetate and hexane to afford 3.74 g (quantitative yield) of the title compound as an oil.

$^1$H-Nuclear magnetic resonance spectrum (400 MHz, CDCl$_3$) δ ppm: 0.96 (3H, doublet, J=6 Hz); 3.80 (1H, doublet, J=12 Hz); 3.94 (1H, singlet); 4.32 (1H, doublet of doublets, J=12, 2 Hz); 4.53 (1H, quartet of doublets, J=6, 3 Hz); 7.09–7.13 (2H, multiplet); 7.46–7.50 (1H, multiplet).

IR spectrum $v_{max}$ (KBr) cm$^{-1}$: 3402, 3174, 1481, 1272, 1104.

Mass spectrum m/z (FAB): 219 (M$^+$+1).

7(iii) (2R,3R)-2-(2,3-Difluorophenyl)-1,3-bis(methanesulfonyloxy)-2-butanol 5.71 g (50 mmol) of methanesulfonyl chloride were added to a solution of 3.51 g (16.1 mmol) of (2R,3 R)-2-(2,3-difluorophenyl)-1,2,3-butanetriol [obtained as described in Step 7(ii) above] in 18 ml of pyridine at 0° C. After stirring the resulting mixture for 0.5 hours, saturated aqueous sodium hydrogen carbonate solution was added to the reaction mixture and the product was extracted with ethyl acetate. The organic layer was washed with dilute hydrochloric acid and then washed with aqueous sodium chloride solution and then concentrated under reduced pressure. The resulting residue was purified by chromatography on a silica gel (100 g) column using a 1:1 mixture of ethyl acetate and hexane as the eluant to afford 5.04g (yield 84%) of the title compound as a colorless oil.

$^1$H-Nuclear magnetic resonance spectrum (400 MHz, CDCl$_3$) δ ppm: 1.28 (3H, doublet, J=7 Hz); 2.99 (3H, singlet); 3.10 (3H, singlet); 3.41 (1H, singlet); 4,75 (2H, doublet, J=1 Hz); 5.31 (1H, quartet, J=7 Hz); 7.16–7.23 (2H, multiplet); 7.46–7.50 (1H, multiplet).

IR spectrum $v_{max}$ (KBr)cm$^{-1}$: 3486, 1485, 1350, 1344, 1171.

Mass spectrum m/z (FAB): 375 (M$^+$+1).

7(iv) (2R,3S)-2-(2,3-Difluorophenyl)-3-methyl-2-[(1H-1,2,4-triazol-1-yl)methyl]oxirane 3.32 g (48.1 mmol) of 1H-1,2,4-triazole were added to a suspension of 1.84 g (41.1 mmol) of a 55% dispersion of sodium hydride in oil in 30 ml of N,N-dimethylformamide at 0° C. with stirring. After the evolution of hydrogen gas had ceased, a solution of 4.50 g (12 mmol) of (2R,3R)-2-(2,3-difluorophenyl)-1,3-bis(methanesulfonyloxy)-2-butanol [prepared as described in Step 7(iii) above] in 13 ml of N,N-dimethylformamide was added to the above reaction mixture. This resulting mixture was stirred at 70° C. for 1.5 hours. After cooling, a saturated aqueous ammonium chloride solution was added to the reaction mixture. The reaction product was extracted with ethyl acetate and the organic layer was washed with water three times and with aqueous sodium chloride solution once and then concentrated under reduced pressure. The resulting residue was purified by chromatography on a silica gel (100 g) column using a 1:1 mixture of ethyl acetate and hexane as the eluant to afford 1.80 g (yield 59%) of the title compound as an oil.

$^1$H-Nuclear magnetic resonance spectrum (400 MHz, CDCl$_3$) δ ppm: 1.66 (3H, doublet, J=6 Hz); 3.23 (1H, quartet, J=6 Hz); 4.46 (1H, doublet, J=15 Hz); 4.91 (1H, doublet, J=15 Hz); 6.79 (1H, double doublet of doublets, J=8, 6, 1 Hz); 6.93 (1H, triple doublet of doublets, J=8, 6, 1 Hz); 7.08 (1H, quartet of doublets, J=8, 1 Hz); 7.82 (1H, singlet); 7.98 (1H, singlet).

IR spectrum $\nu_{max}$ (KBr) cm$^{-1}$: 3111, 1486, 1273, 1136.

Mass spectrum m/z (EI): 251 (M$^+$), 236, 188, 153, 141, 96 (100%).

7(v) (2R,3R)-2-(2,3-Difluorophenyl)-3-[(trans-2-phenyl-1,3-dioxan-5-yl)thio]-1-(1H-1,2,4-triazol-1-yl)-2-butanol 0.29 ml (1.4 mmol) of a 4.9 M solution of sodium methoxide in methanol were added to a solution of 1.77 g (7.1 mmol) of (2R,3S)-2-(2,3-difluorophenyl)-3-methyl-2-[(1H-1,2,4-triazol-1-yl)methyl]oxirane [prepared as described in Step 7(iv) above] and 2.20 g (9.2 mmol) of trans-5-(acetylthio)-2-phenyl-1,3-dioxane [prepared as described in Japanese Patent Application (Kokai) Hei 8-333350] in 20 ml of ethanol. The resulting mixture was then heated under reflux for 7 hours. After cooling the reaction mixture, it was partitioned between ethyl acetate and an aqueous ammonium chloride solution. The organic layer was washed with saturated aqueous sodium chloride solution and concentrated under reduced pressure to afford 3.65 g of the crude title compound. An aliquot (0.28 g) of the crude residue was purified by chromatography on a silica gel (15 g) column using a 2:5 mixture of ethyl acetate and hexane as eluent to afford 0.21 g of the title compound.

1H-Nuclear magnetic resonance spectrum (400 MHz, CDCl$_3$) δ ppm: 1.23 (3H, doublet, J=7 Hz); 3.39 (1H, quartet, J=7 Hz); 3.50 (1H, triplet of triplets, J=11, 5 Hz); 3.75 (1H, triplet, J=11 Hz); 3.77 (1H, triplet, J=11 Hz); 4.40 (1H, double doublet of doublets, J=11, 5, 2 Hz); 4.52 (1H, double doublet of doublets, J=11, 5, 2 Hz); 4.87 (1H, doublet, J=14, 6 Hz); 5.08 (1H, doublet, J=14 Hz); 5.12 (1H, doublet, J=1 Hz); 5.49 (1H, singlet); 6.92–6.98 (1H, multiplet); 7.05 (1H, quartet of doublets, J=8, 1 Hz); 7.11–7.16 (=H, multiplet); 7.34–7.41 (3H, multiplet); 7.49 (2H, doublet of doublets, J=7, 3 Hz); 7.79 (1H, singlet); 7.82 (1H, singlet).

IR spectrum $\nu_{max}$ (KBr) cm$^{-1}$: 3405, 1480, 1275, 1140, 1075.

Mass spectrum m/z (FAB): 448 (M$^+$+1).

7(vi) (2R,3R)-2-(2,3-difluorophenyl)-3-[[1-(hydroxymethyl)-2-hydroxyethyl]thio]-1-(1H-1,2,4-triazol-1-yl)-2-butanol 30 ml (30 mmol) of 1 N hydrochloric acid were added to a solution of 3.35 g of crude (2R,3R)-2-(2,3-difluorophenyl)-3-[(trans-2-phenyl-1,3-dioxan-5-yl)thio]-1-(1H-1,2,4-triazol-1-yl)-2-butanol [prepared as described in Step 7(v) above] in 45 ml of toluene. The resulting mixture was heated at 50° C. for 6 hours. At the end of this time, the aqueous layer was separated. The oily layer was then extracted twice with a dilute hydrochloric acid solution. The aqueous layers were then combined and sodium hydrogen carbonate was carefully added in small portions to the solution until the evolution of carbon dioxide gas had ceased. The reaction mixture was then extracted with ethyl acetate and the extract was concentrated under reduced pressure to afford the title compound as a solid. The solid was washed with a 2:1 mixture of ethyl acetate and hexane and 1.54 g [overall yield from Step 7(v) 61%] of the title compound were collected by filtration.

$^1$H-Nuclear magnetic resonance spectrum (400 MHz, DMSO) δ ppm: 1.06 (3H, doublet, J=7 Hz); 2.85 (1H, quintet, J=6 Hz); 3.55–3.68 (5H, multiplet); 4.80 (1H, doublet, J=15 Hz); 4.85 (1H, triplet, J=5 Hz); 5.04 (1H, triplet, J=5 Hz); 5.10 (1H, doublet, J=15 Hz); 6.01 (1H, singlet); 6.97–7.01 (2H, multiplet); 7.23–7.30 (1H, multiplet); 7.62 (1H, singlet); 8.31 (1H, singlet).

IR spectrum $\nu_{max}$ (KBr) cm$^{-1}$: 3238, 1480, 1272, 1206, 1138.

Mass spectrum m/z (FAB): 360 (M$^+$+1).

7(vii) (2R,3R)-3-[[trans-2-[(1E,3E)-4-(4-Cyano-2-fluorophenyl)-1,3-butadien-1-yl]-1,3-dioxan-5-yl]thio]-2-(2,3-difluorophenyl)-1-(1H-1,2,4-triazol-1-yl)-2-butanol Crude title compound was obtained as an oil in a similar manner to that described in Example 1(iii) above using 643.3 mg (1.80 mmol) of (2R,3R)-2-(2,3-difluorophenyl)-3-[[1-(hydroxymethyl)-2-hydroxyethyl]thio]-1-(1H-1,2,4-triazol-1-yl)-2-butanol [prepared as described in Step 7(vi) above], 361.8 mg (1.80 mmol) of 3-fluoro-4-[(1E,3E)-5-oxo-1,3-pentadienyl]-benzonitrile [prepared as described in Example 1(ii) above] and 376.3 mg (1.98 mmol) of p-toluenesulfonic acid monohydrate. The oil was purified by chromatography on a silica gel (50 g) column using a 1:1 mixture of ethyl acetate and hexane as the eluant to give 533.7 mg (yield 55%) of the title compound as a colorless non-crystalline solid.

$^1$H-Nuclear magnetic resonance spectrum (400 MHz, CDCl$_3$) δ ppm 1.21 (3H, doublet, J=7 Hz); 3.36 (1H, quartet, J=7 Hz); 3.43 (1H, triplet of triplets, J=11, 5 Hz); 3.62 (1H, triplet, J=11 Hz); 3.64 (1H, triplet, J=11 Hz); 4.32 (1H, double doublet of doublets, J=11, 5, 2 Hz); 4.43 (1H, double doublet of doublets, J=1, 5, 2 Hz); 4.85 (1H, doublet, J=14 Hz); 5.06 (1H, doublet, J=14 Hz); 5.07 (1H, doublet, J=4 Hz); 5.12 (1H, singlet); 5.90 (1H, doublet of doublets, J=15, 4 Hz); 6.62 (1H, doublet of doublets, J=15, 10 Hz); 6.75 (1H, doublet, J=16 Hz); 6.92–6.99 (2H, multiplet); 7.01–7.08 (1H, multiplet); 7.10–7.14 (1H, multiplet); 7.34 (1H, doublet of doublets, J=10, 1 Hz); 7.41 (1H, doublet of doublets, J=8, 1 Hz); 7.58 (1H, triplet, J=8 Hz); 7.79 (1H, singlet); 7.82 (1H, singlet).

IR spectrum $\nu_{max}$ (KBr) cm$^{-1}$: 3406, 2331, 1480, 1275, 1140.

Mass spectrum m/z (FAB): 543 (M$^+$+1).

EXAMPLE 8

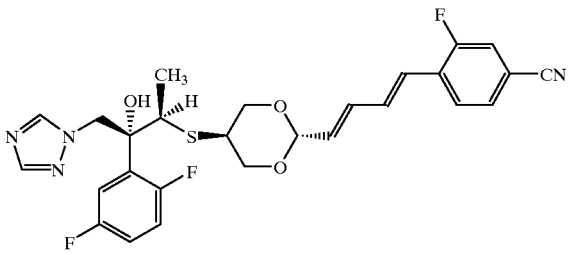

8(i) (2R)-2',5'-Difluoro-2-(3,4,5,6-tetrahydro-2H-pyran-2-yloxy)propiophenone 6.50 g (yield 98%) of the title compound were obtained as an oil according to the reaction and treatment described in Example 7(i) above using 7.04 g (36.5 mmol) of 1-bromo-2,5-difluorobenzene and 6.0 g (25 mmol) of 4-[(2R)-2-(3,4,5,6-tetrahydro-2H-pyran-2-yloxy)propionyl]morpholine [prepared as described in Chem. Pharm. Bull., 41, 1035–1042 (1993)].

$^1$H-Nuclear magnetic resonance spectrum (400 MHz, CDCl$_3$) δ ppm: 1.43 [(3/2)H, doublet of doublets, J=6, 1 Hz]; 1.48 [(3/2)H, doublet of doublets, J=7, 1 Hz]; 1.50–1.89 (6H, multiplet); 3.36 [(1/2)H, doublet of triplets, J=12, 4 Hz]; 3.53 [(1/2)H, doublet of triplets, J=12, 4 Hz]; 3.73 [(1/2)H, doublet of triplets, J=12, 4 Hz]; 3.90 [(1/2)H, doublet of triplets, J=11, 4 Hz]; 4.66 [(1/2)H, triplet, J=4 Hz]; 4.75 [(1/2)H, triplet, J=4 Hz]; 4.87 [(1/2)H, quartet of doublets, J=7, 1 Hz]; 5.12 [(1/2)H, quartet of doublets. J=7, 2 Hz); 7.08–7.15 (1H, multiplet); 7.17–7.25 (1H, multiplet); 7.50–7.54 (1H, multiplet).

IR spectrum ν$_{max}$ (CHCl$_3$) cm$^{-1}$: 1698, 1491, 1417, 1257.

Mass spectrum m/z (FAB); 271 (M$^+$+1).

8(ii) (2R,3R)-2-(2,5-Difluorophenyl)-1,2,3-butanetriol 4.90 g (yield 95%) of the title compound were obtained as an oil according to the reaction of Example 7(ii) above using 6.40 g (23.7 mmol) of (2R)-2',5'-difluoro-2-(3,4,5,6-tetrahydro-2H-pyran-2-yloxy)propiophenone [prepared as described in Step 8(i) above] and 7.90 g (47.4 mmol) of (dimethylisopropoxysilyl)methylmagnesium chloride in the first step of the reaction, 22 ml of a 31% solution of hydrogen peroxide and 1.8 g (21 mmol) of sodium hydrogen carbonate in the second step and 0.3 g (1.57 mmol) of p-toluensulfonic acid monohydrate in the third step of the reaction followed by purification of the reaction product by chromatography on a silica gel (100 g) column using a 1:2 to 1:0 mixture of ethyl acetate and hexane as the eluant.

$^1$H-Nuclear magnetic resonance spectrum (400 MHz, CDCl$_3$) δ ppm: 0.95 (3H, doublet, J=6 Hz); 3.77 (1H, doublet, J=11 Hz); 4.31 (1H, doublet of doublets, J=11, 2 Hz); 4.52 (1H, quartet of doublets, J=6, 3 Hz); 6.94–7.00 (2H, multiplet); 7.44–7.48 (1H, multiplet).

IR spectrum ν$_{max}$ (KBr) cm$^{-1}$: 3422, 1487, 1142, 1065.

Mass spectrum m/z (FAB): 219 (M$^+$+1).

8(iii) (2R,3R)-2-(2,5-Difluoronhenyl)-1,3-bis(methanesulfonyl)-2-butanol

In the same manner as that described in Example 7(iii) above, 4.80 g (10.1 mmol) of (2R,3R)-2-(2,5-difluorophenyl)-1,2,3-butanetriol [prepared as described in Step 8(ii) above] were reacted with 7.75 g (67.8 mmol) of methanesulfonyl chloride and the resulting product was purified by chromatography on a silica gel (110 g) column using a 1:2 to 1:1 mixture of ethyl acetate and hexane as the eluant to afford 7.56 g (yield 92%) of the title compound as a colorless oil.

$^1$H-Nuclear magnetic resonance spectrum (400 MHz, CDCl$_3$) δ ppm: 1.27 (3H, doublet, J=6 Hz); 2.99 (3H, singlet); 3.11 (3H, singlet); 3.36 (1H, singlet); 4.73 (2H. singlet); 5.32 (1H, quartet, J=7 Hz); 7.03–7.26 (2H, multiplet); 7.43–7.47 (1H, multiplet).

IR spectrum ν$_{max}$ (KBr) cm$^{-1}$: 3484, 1492, 1346, 1169.

Mass spectrum m/z (FAB): 375 (M$^+$+1).

8(iv) (2R,3S)-2-(2,5-Difluorophenyl)-3-methyl-2-[(1H-1,2,4-triazol-1-yl)methyl]oxirane In the same manner as that described in Example 7(iv) above, 7.00 g (18.7 mmol) of (2R,3R)-2-(2,5-difluorophenyl)-1,3-bis(methanesulfonyl)-2-butanol [prepared as described in Step 8(iii) above] were reacted with 1H-1,2,4-triazole and the reaction product was purified by chromatography on a silica gel (100 g) column using a 1:1 to 3:2 mixture of ethyl acetate and hexane as the eluant to afford 2.65 g (yield 56%) of the title compound as an oil.

$^1$H-Nuclear magnetic resonance spectrum (400 MHz, CDCl$_3$) δ ppm: 1.64 (3H, doublet, J=6 Hz): 3.20 (1H, quartet, J=6 Hz): 4.42 (1H, doublet, J=15 Hz); 4.97 (1H, doublet, J=15 Hz); 6.76–6.81 (1H, multiplet); 6.89–6.96 (1H, multiplet); 6.99 (1H, doublet of triplets, J=9, 4 Hz); 7.83 (1H, singlet); 7.99 (1H, singlet).

IR spectrum ν$_{max}$ (KBr)cm$^{-1}$: 3110, 1500, 1490, 1184, 1135.

Mass spectrum m/z (EI): 251 (M$^+$).

8(v) (2R,3R)-2-(2,5-Difluorophenyl)-3-[(trans-2-phenyl-1,3-dioxan-5-yl)thio]-1-(1H-1,2,4-triazol-1-yl)-2-butanol In the same manner as that described in Example 7(v) above, 2.59 g (10.3 mmol) of (2R,3 S)-2-(2,5-difluorophenyl)-3-methyl-2-[(1H-1,2,4-triazol-1-yl)methyl]oxirane [prepared as described in Step 8(iv) above] were reacted with 3.19 g (13.4 mmol) of trans-5-(acetylthio)-2-phenyl-1,3-dioxane [prepared as described in Japanese Patent Application (Kokai) Hei 8-333350] to afford 5.36 g of the crude title compound. 0.27 g of the purified title compound were obtained as a non-crystalline solid by chromatography of 0.36 g of the crude product on a silica gel (20 g) column using a 1:1 mixture of ethyl acetate and hexane as the eluant.

$^1$H-Nuclear magnetic resonance spectrum (400 MHz, CDCl$_3$) δ ppm: 1.22 (3H, doublet, J=7 Hz); 3.38 (1H, quartet, J=7 Hz); 3.49 (1H, triplet of triplets, J=12, 5 Hz); 3.75 (1H, triplet, J=12 Hz); 3.77 (1H, triplet, J=12 Hz); 4.41 (1H, double doublet of doublets, J=12, 5, 2 Hz); 4.52 (1H, double doublet of doublets, J=12, 5, 2 Hz); 4.88 (1H, doublet, J=14 Hz); 5.06 (1H, doublet, J=14 Hz); 5.08 (1H, doublet, J=1 Hz); 5.49 (1H, singlet); 6.85–6.91 (1H, multiplet); 6.95 (1H, doublet of triplets, J=9, 4 Hz); 7.08–7.13 (3H, multiplet); 7.36–7.41 (2H, multiplet); 7.49 (1H, doublet of doublets, J=7, 2 Hz); 7.80 (1H, singlet); 7.82 (1H, singlet).

IR spectrum ν$_{max}$ (KBr) cm$^{-1}$: 3405, 1487, 1140, 1074.

Mass spectrum m/z (FAB): 448 (M$^+$+1).

8(vi) (2R,3R)-2-(2,5-Difluorophenyl)-3-[[1-(hydroxymethyl)-2-hydroxyethyl]thio]-1-(1H-1,2,4-triazol-1-yl)-2-butanol In the same manner as that described in Example 7(vi) above, 5.0 g of crude (2R,3R)-2-(2,5-difluorophenyl)-3-

[(trans-2-phenyl-1,3-dioxan-5-yl)thio]-1-(1H-1,2,4-triazol-1-yl)-2-butanol [prepared as described in Step 8(v) above] were treated with hydrochloric acid and the product obtained was purified by chromatography on a silica gel (50 g) column using a 3:100 mixture of methanol and ethyl acetate as the eluant to afford 3.17 g [overall yield from Step 8(v) 83%] of the of the title compound as an oil.

$^1$H-Nuclear magnetic resonance spectrum (400 MHz, CDCl$_3$) δ ppm: 1.22 (3H, doublet, J=7 Hz); 3.27 (1H, quintet, J=6 Hz); 3.50 (1H, quartet, J=7 Hz); 3.75 (1H, doublet of doublets, J=11, 6 Hz); 3.78–3.86 (2H, multiplet); 3.96 (1H, doublet of doublets, J=11, 6 Hz); 4.89 (1H, doublet, J=14 Hz); 5.19 (1H, doublet, J=14 Hz); 5.56 (1H, singlet); 6.87–7.00 (2H, multiplet); 7.16–7.11 (1H, multiplet); 7.78 (1H, singlet); 7.88 (1H, singlet).

IR spectrum ν$_{max}$ (KBr) cm$^{-1}$: 3302, 1488, 1047.

Mass spectrum m/z (FAB): 360 (M$^+$+1).

8(vii) (2R,3R)-3-[[trans-2-[(1E,3E)-4-(4-Cyano-2-fluorophenyl)-1,3-butadien-1-yl]-1,3-dioxan-5-yl]thio]-2-(2,5-difluorophenyl)-1-(1H-1,2,4-triazol-1-yl)-2-butanol In the same manner as that described in Example 1(iii) above, a reaction was carried out using 1.02 g (2.84 mmol) of (2R,3R)-2-(2,5-difluorophenyl)-3-[[1-(hydroxymethyl)-2-hydroxyethyl]thio]-1-(1H-1,2,4-triazol-1-yl)-2-butanol [prepared as described in Step 8(vi) above], 571.6 mg (2.84 mmol) of 3-fluoro-4-[(1E,3E)-5-oxo-1,3-pentadienyl]benzonitrile and 594.5 mg (3.13 mmol) of p-toluenesulfonic acid monohydrate and the reaction product was purified by chromatography on a silica gel (75 g) column using a 1:1 mixture of ethyl acetate and hexane as the eluant to give 1.03 g (yield 66%) of the title compound as a colorless non-crystalline solid.

$^1$H-Nuclear magnetic resonance spectrum (400 MHz, CDCl$_3$) δ ppm: 1.20 (3H, doublet, J=7 Hz); 3.35 (1H, quartet, J=7 Hz); 3.41 (1H, triplet of triplets, J=11, 5 Hz); 3.62 (1H, triplet, J=11 Hz); 3.64 (1H, triplet, J=11 Hz); 4.31 (1H, double doublet of doublets, J=11, 5, 2 Hz); 4.43 (1H, double doublet of doublets, J=11, 5, 2 Hz); 4.86 (1H, doublet, J=14 Hz); 5.03 (1H, doublet, J=14 Hz); 5.06–5.08 (2H, multiplet); 5.90 (1H, doublet of doublets, J=15, 4 Hz); 6.62 (1H, doublet of doublets, J=15, 10 Hz); 6.75 (1H, doublet, J=16 Hz); 6.95 (1H, doublet of doublets, J=16, 10 Hz); 6.85–6.98 (2H, multiplet); 7.07–7.12 (1H, multiplet); 7.34 (1H, doublet, J=10 Hz); 7.40 (1H, doublet, J=8 Hz); 7.58 (1H, triplet, J=8 Hz); 7.79 (1H, singlet); 7.81 (1H, singlet).

IR spectrum ν$_{max}$ (KBr) cm$^{-1}$: 3416, 2231, 1487, 1141.

Mass spectrum m/z (FAB): 543 (M$^+$+1).

EXAMPLE 9

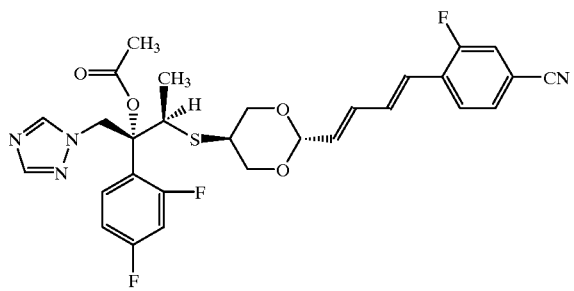

543 mg (1.00 mmol) of (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol (prepared as described in Examples 1 or 4 above) were added to a suspension of 48 mg (1.10 mmol) of a 55% dispersion of sodium hydride (which had been pre-washed with hexane) in 5 ml of N,N-dimethylformamide at ambient temperature with stirring. After the evolution of hydrogen gas had ceased. the mixture was cooled to 0° C. and then 117.8 mg (1.50 mmol) of acetyl chloride were added to the reaction mixture. This resulting mixture was stirred at 70° C. for 28 hours. After cooling to ambient temperature. the reaction mixture was partitioned between ethyl acetate and a saturated aqueous ammonium chloride solution. The organic layer was washed with water and aqueous sodium chloride solution and then concentrated under reduced pressure. The oily residue thus obtained was purified by chromatography on a silica gel (50 g) column using a 1:2 to 2:1 mixture of ethyl acetate and hexane as the eluant to afford 226.2 mg of an oil containing a mixture of the title compound and the starting material in a ratio of 7:3. The oil was further purified by chromatography recycled 18 times in recycle HPLC [JAIGEL-1H (20 mm i.d.×600 mm) and JAIGEL-2H (20 mm i.d.×600 mm), which are products of Japan Analytical Industry, Co. Ltd., were combined in series] using chloroform as the eluant to give 120 mg (yield 21%) of the title compound as a non-crystalline solid.

$^1$H-Nuclear magnetic resonance spectrum (400 MHz, CDCl$_3$) δ ppm: 1.35 (3H, doublet of doublets, J=7, 2 Hz); 2.11 (3H, singlet); 3.08 (1H, triplet of triplets, J=11, 5 Hz); 3.52 (2H, triplet, J=11 Hz); 3.92 (1H, quartet, J=7 Hz); 4.15–4.23 (2H, multiplet); 5.00 (1H, doublet, J=4 Hz); 5.32 (1H, doublet of doublets, J=15, 3 Hz); 5.38 (1H, doublet, J=15 Hz); 5.85 (1H, doublet of doublets, J=15, 4 Hz); 6.58 (1H, doublet of doublets, J=15, 12 Hz); 6.74 (1H, doublet, J=15 Hz); 6.85–6.98 (3H, multiplet); 7.28–7.36 (3H, multiplet); 7.57 (1H, doublet of triplets, J=8, 4 Hz); 7.94 (1H, singlet); 7.95 (1H, singlet).

IR spectrum ν$_{max}$ (KBr) cm$^{-1}$: 2231, 1746, 1504, 1141.

Mass spectrum m/z (FAB): 585 (M$^+$+1).

EXAMPLE 10

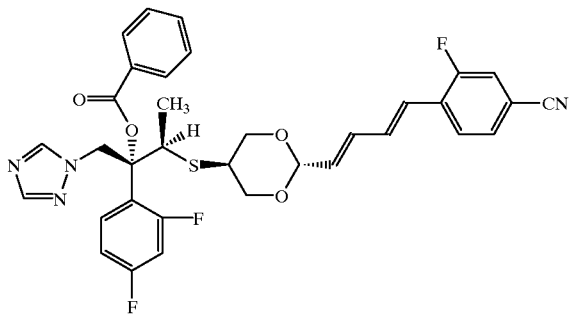

543 mg (1.00 mmol) of (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol (prepared as described in Examples 1 or 4 above) were added to a suspension of 48 mg (1.10 mmol) of a 55% dispersion of sodium hydride in oil (which had been pre-washed with hexane) in 3 ml of N,N-dimethylformamide at ambient temperature with stirring. After the evolution of hydrogen gas had ceased, 210.9 mg (1.50 mmol) of benzoyl chloride were added to the mixture. The resulting mixture was stirred at ambient temperature for 6 hours. At the end of this time, the reaction mixture was partitioned between ethyl acetate and a saturated aqueous sodium hydrogen carbonate solution. The organic layer was washed with water and an aqueous sodium chloride solution and then concentrated under reduced pressure. The oily residue thus obtained was purified by chromatography on a silica gel (40 g) column using a 1:1 mixture of ethyl acetate and hexane as the eluant to give 234.2 mg (yield 36%) of the title compound as a colorless non-crystalline solid.

$^1$H-Nuclear magnetic resonance spectrum (400 MHz, CDCl$_3$) δ ppm: 1.47 (3H, doublet of doublets, J=7, 2 Hz); 3.08 (1H, multiplet); 3.53 (1H, triplet, J=11 Hz); 3.54 (1H, triplet, J=11 Hz); 4.03 (1H, quartet, J=7 Hz); 4.18–4.22 (2H, multiplet); 5.01 (1H, doublet, J=4 Hz); 5.50 (1H, doublet of doublets, J=15, 3 Hz); 5.55 (1H, doublet, J=15 Hz); 5.86 (1H, doublet of doublets, J=15, 4 Hz); 6.59 (1H, doublet, J=15, 10 Hz); 6.74 (1H, doublet, J=16 Hz); 6.88–6.97 (3H, multiplet); 7.34 (1H, doublet, J=10 Hz); 7.40–7.50 (4H, multiplet); 7.56–7.64 (2H, multiplet); 7.86 (1H, singlet); 7.89 (1H, singlet); 7.94 (2H, doublet, J=8 Hz).

IR spectrum v$_{max}$ (KBr) cm$^{-1}$: 2231, 1724, 1504, 1276.

Mass spectrum m/z (FAB): 647 (M$^+$+1).

EXAMPLE 11

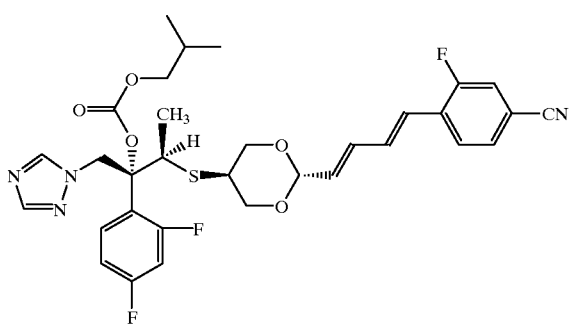

543 mg (1.00 mmol) of (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol (prepared as described in Examples 1 or 4 above) were added to a suspension of 48 mg (1.10 mmol) of a 55% dispersion of sodium hydride in oil (which had been pre-washed with hexane) in 3 ml of N,N-dimethylformamide at 0° C. with stirring and then the resulting mixture was stirred at ambient temperature. After the evolution of hydrogen gas had ceased, the reaction mixture was cooled to 0° C. and then 204.9 mg (1.50 mmol) of isobutyl chloroformate were added to the mixture. The resulting mixture was stirred at ambient temperature for 2 hours. At the end of this time, the reaction mixture was partitioned between ethyl acetate and a saturated aqueous ammonium chloride solution. The organic layer was washed with water and an aqueous sodium chloride solution and then concentrated under reduced pressure. The resulting oily residue was purified by chromatography on a silica gel (25 g) column using a 1:2 mixture of ethyl acetate and hexane as the eluant to give 192.3 mg (yield 30%) of the title compound as a colorless non-crystalline solid.

$^1$H-Nuclear magnetic resonance spectrum (400 MHz, CDCl$_3$) δ ppm: 0.95 (3H, doublet, J=7 Hz); 0.97 (3H, doublet, J=7 Hz); 1.34 (3H, doublet of doublets, J=7, 2 Hz); 3.05 (1H, triplet of triplets, J=12, 5 Hz); 3.49 (1H, triplet, J=12 Hz); 3.50 (1H, triplet, J=12 Hz); 3.89–3.99 (3H, multiplet); 4.19 (1H, double doublet of doublets, J=12, 5, 2 Hz); 4.34 (1H, double doublet of doublets, J=12, 5, 2 Hz); 4.97 (1H, doublet, J=4 Hz); 5.34 (1H, doublet of doublets, J=15, 4 Hz); 5.43 (1H, doublet, J=15 Hz); 5.86 (1H, doublet of doublets, J=15, 4 Hz); 6.58 (1H, doublet of doublets, J=15, 10 Hz); 6.73 (1H, doublet, J=15 Hz); 6.92 (1H, doublet of doublets, J=15, 10 Hz); 6.85–6.96 (2H, multiplet); 7.33 (1H, doublet, J=10 Hz); 7.40 (1H, doublet, J=7 Hz); 7.45 (1H, doublet of triplets, J=8, 2 Hz); 7.57 (1H, triplet, J=8 Hz); 7.95 (1H, singlet); 7.97 (1H, singlet).

IR spectrum v$_{max}$ (KBr) cm$^{-1}$: 2231, 1749, 1504, 1141.

Mass spectrum m/z (FAB): 643 (M$^+$+1).

EXAMPLE 12

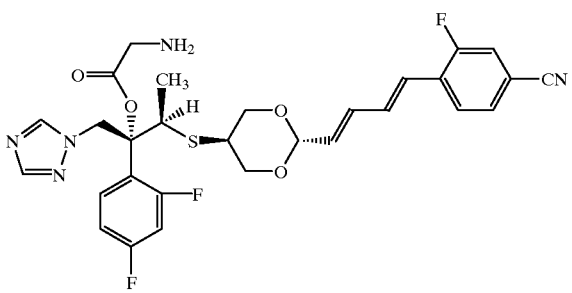

12(i) [(1R,2R)-2-[[trans-2-[(1E,3E)-4-(4-Cyano-2-fluorophenyl)-1,3-butadien-1-yl]-1,3-dioxan-5-yl]thio]-1-(2,4-difluorophenyl)-1-[(1H-1,2,4-triazol-1-yl)methyl]propyl](1,3-dioxo-1,3-dihydro-2-isoindolyl)acetate 280 mg (2.2 mmol) of oxalyl chloride and 15 μl of N,N-dimethylformamide were added to a suspension of 410 mg (2.0 mmol) of N-phthaloylglycine in 10 ml of dichloromethane at 0° C. with stirring. After stirring this mixture at ambient temperature for 3 hours, solvent was removed from the reaction mixture by evaporation under reduced pressure and then the mixture was evaporated to dryness in vacuo to afford the crude acid chloride as a solid.

542 mg (1.00 mmol) of (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol (prepared as described in Examples 1 or 4) were added to a suspension of 87 mg (2.00 mmol) of a 55% dispersion of sodium hydride in oil (which had been pre-washed with hexane) in 5 ml of N,N-dimethylformamide at 0° C. with stirring and then the mixture was stirred at ambient temperature for 40 minutes. After the reaction mixture was cooled to 0° C., a solution of the crude acid chloride obtained above in 4 ml of tetrahydrofuran was added to the mixture. The resulting mixture was stirred at ambient temperature for 1 hour. At the end of this time, the reaction mixture was partitioned between ethyl acetate and water. The organic layer was washed consecutively with a saturated aqueous sodium hydrogen carbonate solution, a 10% aqueous sodium chloride solution and a saturated aqueous sodium chloride solution and then concentrated under reduced pressure. The oily residue thus obtained was purified by chromatography on a silica gel (10 g) column using a 1:1 mixture of ethyl acetate and hexane as the eluant to give 187 mg (yield 26%) of the title compound as an oil.

$^1$H-Nuclear magnetic resonance spectrum (400 MHz, CDCl$_3$) δ ppm: 1.37 (3H, doublet of doublets, J=7, 2 Hz); 2.99 (1H, triplet of triplets, J=11, 5 Hz); 3.47 (1H, triplet, J=11 Hz); 3.48 (1H, triplet, J=11 Hz); 3.82 (1H, quartet, J=7 Hz); 4.1–4.2 (2H, multiplet); 4.45 (1H, doublet, J=17 Hz); 4.57 (1H, doublet, J=17 Hz); 4.97 (1H, doublet, J=4 Hz); 5.33 (1H, doublet, J=15 Hz); 5.37 (1H, doublet of doublets, J=15, 2 Hz); 5.84 (1H, doublet, J=15, 4 Hz); 6.58 (1H, doublet of doublets, J=15, 11 Hz); 6.74 (1H, doublet, J=16 Hz); 6.8–7.0 (2H, multiplet); 6.92 (1H, doublet of doublets, J=16, 11 Hz); 7.33 (1H, doublet of doublets, J=10, 2 Hz); 7.35–7.45 (2H, multiplet); 7.57 (1H, triplet, J=8 Hz); 7.77 (2H, doublet of doublets, J=6, 3 Hz); 7.91 (2H, doublet of doublets, J=6,3 Hz); 7.99 (1H, singlet); 8.12 (1H, singlet).

IR spectrum $v_{max}$ (KBr) cm$^{-1}$: 2233, 1726, 1504, 1417.

Mass spectrum m/z (FAB): 730 (M$^+$+1).

Specific rotation: [α]$_D^{25}$+5.5° (c=1.02, CHCl$_3$).

12(ii) [(1R,2R)-2-[[trans-2-[(1E,3E)-4-(4-Cyano-2-fluorophenyl)-1,3-butadien-1-yl]-1,3-dioxan-5-yl]thio]-1-(2,4-difluorophenyl)-1-](1H-1,2,4-triazol-1-yl)methyl]propyl]aminoacetate 104 mg (2.22 mmol) of methylhydrazine were added to a solution of 180 mg (0.25 mmol) of [(1R,2R)-2-[[trans-2-[(1E,3E)-4-(4-cyano-2-fluorophenyl)-1,3-butadien-1-yl]-1,3-dioxan-5-yl]thio]-1-(2,4-difluorophenyl)-1-[(1H-1,2,4-triazol-1-yl)methyl]propyl](1,3-dioxo-1,3-dihydro-2-isoindolyl)acetate [prepared as described in Step 12(i) above] in 5 ml of dichloromethane in an ice bath. The resulting mixture was stirred at ambient temperature for 5 hours. At the end of this time, the reaction mixture was concentrated and evaporated to dryness in vacuo. Dichloromethane was added to the resulting residue and the dichloromethane was then evaporated under reduced pressure. The resulting residue was dissolved in dichloromethane, the solution was allowed to stand at ambient temperature for 12 hours, and was then concentrated. The resulting residue was purified by chromatography on a silica gel (5 g) column using a 9:1 mixture of ethyl acetate and ethanol as the eluant to give 126 mg (yield 85%) of the title compound as a pale yellow non-crystalline solid.

$^1$H-Nuclear magnetic resonance spectrum (400 MHz, CDCl$_3$) δ ppm: 1.35 (3H, doublet of doublets, J=7, 2 Hz); 3.04 (1H, triplet of triplets, J=11, 5 Hz); 3.4–3.5 (4H, multiplet); 3.90 (1H, quartet, J=7 Hz); 4.1–4.3 (2H, multiplet); 5.00 (1H, doublet, J=4 Hz); 5.36 (1H, doublet, J=15 Hz); 5.38 (1H, doublet of doublets, J=15, 2 Hz); 5.85 (1H, doublet of doublets, J=15, 4 Hz); 6.59 (1H, doublet of doublets, J=15, 10 Hz); 6.74 (1H, doublet, J=16 Hz); 6.80–6.95 (3H, multiplet); 7.3–7.4 (2H, multiplet); 7.40 (1H, doublet of doublets. J=8, 1 Hz); 7.57 (1H, triplet, J=8 Hz); 7.91 (1H, singlet); 7.92 (1H, singlet).

IR spectrum $v_{max}$ (CHCl$_3$) cm$^{-1}$: 2233, 1748, 1615, 1504, 1276, 1140.

Mass spectrum m/z (FAB): 600 (M$^+$+1).

Specific rotation: [α]$_D^{25}$+14.6° (c=0.52, CHCl$_3$).

EXAMPLE 13

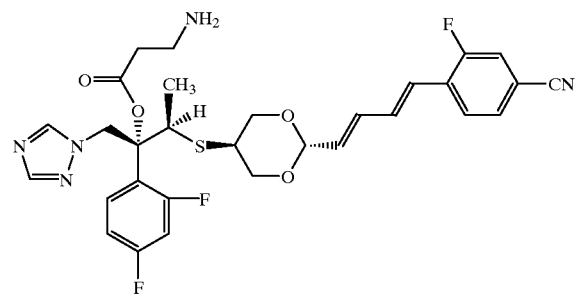

13(i) [(1R,2R)-2-[[trans-2-[(1E,3E)-4-(4-Cyano-2-fluorophenyl)-1,3-butadien-1-yl]-1,3-dioxan-5-yl]thio]-1-(2,4-difluorolphenyl)-1-[(1H-1,2,4-triazol-1-yl)methyl]propyl]3-(1,3-dioxo-1,3-dihydro-2-isoindolyl)propionate 280 mg (2.2 mmol) of oxalyl chloride and 15 μl of N,N-dimethylformamide were added to a suspension of 438.4 mg (2.0 mmol) of N-phthaloyl-β-alanine [prepared as described in J.Agric. Food Chem., 47, 1276–1284 (1999)] in 3 ml of dichloromethane with stirring. After stirring this mixture at ambient temperature for 40 minutes, the solvent was removed from the reaction mixture by evaporation under reduced pressure and then evaporated to dryness in vacuo to afford the crude acid chloride as a solid.

543 mg (1.00 mmol) of (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol (prepared as described in Examples 1 or 4) were added to a suspension of 48 mg (1.10 mmol) of a 55% dispersion of sodium hydride in oil (which had been pre-washed with hexane) in 5 ml of N,N-dimethylformamide at 0° C. with stirring and then the resulting mixture was stirred at ambient temperature for 20 minutes. After the reaction mixture was cooled to 0° C., a solution of the crude acid chloride obtained above in 4 ml of tetrahydrofuran was added to the reaction mixture. The resulting mixture was stirred at ambient temperature for 1 hour. At the end of this time, the reaction mixture was partitioned between ethyl acetate and a saturated aqueous ammonium chloride solution. The organic layer was washed with water, then with a saturated aqueous sodium chloride solution and then concentrated under reduced pressure. The resulting oily residue was purified by chromatography on a silica gel (40 g) column using a 1:1 mixture of ethyl acetate ethyl acetate and hexane as the eluant to give 100 mg (yield 13%) of the title compound as an oil.

$^1$H-Nuclear magnetic resonance spectrum (400 MHz, CDCl$_3$) δ ppm: 1.33 (3H, doublet of doublets, J=7, 2 Hz);

2.82 (1H, triplet of doublets, J=7, 1 Hz); 2.92 (1H, triplet, J=7 Hz); 2.95–3.03 (1H, multiplet); 3.47 (1H, triplet, J=11 Hz); 3.49 (1H, triplet, J=11 Hz); 3.85 (1H, quartet, J=7 Hz); 3.94–4.00 (2H, multiplet); 4.05–4.11 (2H, multiplet); 4.97 (1H, doublet, J=4 Hz); 5.31 (1H, doublet, J=15 Hz); 5.35 (1H, doublet, J=15 Hz); 5.84 (1H, doublet of doublets, J=15, 4 Hz); 6.57 (1H, doublet of doublets, J=15, 10 Hz); 6.73 (1H, doublet, J=16 Hz); 6.77–6.85 (2H, multiplet); 6.92 (1H, doublet of doublets, J=16, 10 Hz); 7.29–7.35 (2H, multiplet); 7.40 (1H, doublet of doublets, J=8, 1 Hz); 7.57 (1H, triplet, J=8 Hz); 7.71–7.75 (2H, multiplet); 7.83–7.89 (2H, multiplet); 7.86 (1H, singlet); 7.97 (1H, singlet).

13(ii) [(1R,2R)-2-[[trans-2-[(1E,3E)-4-(4-Cyano-2-fluorophenyl)-1,3-butadien-1-yl]-1,3-dioxan-5-yl]thio]-1-(2,4-difluorophenyl)-1-[(1H-1,2,4-triazol-1-yl)methyl]propyl]3-aminopropionate 222.7 mg (4.38 mmol) of methylhydrazine were added to a solution of 100 mg (0.13 mmol) of [(1R,2R)-2-[[trans-2-[(1E,3E)-4-(4-cyano-2-fluorophenyl)-1,3-butadien-1-yl]-1,3-dioxan-5-yl]thio]-1-(2,4-difluorophenyl)-1-[(1H-1,2,4-triazol-1-yl)methyl]propyl]3-(1,3-dioxo-1,3-dihydro-2-isoindolyl)propionate [prepared as described in Step 13(i) above] in 2 ml of dichloromethane in an ice bath. The resulting mixture was stirred at ambient temperature for 20 hours. At the end of this time, the reaction mixture was concentrated and then evaporated to dryness in vacuo. Dichloromethane was added to the resulting residue and the dichloromethane was then evaporated under reduced pressure. The resulting residue was then dissolved in dichloromethane, the solution was allowed to stand at ambient temperature for 12 hours and then concentrated. The residue thus obtained was purified by chromatography on a silica gel (15 g) column using a 9:1 mixture of ethyl acetate and methanol to give 41.5 mg (yield 50%) of the title compound as a pale yellow non-crystalline solid.

$^1$H-Nuclear magnetic resonance spectrum (400 MHz, CDCl$_3$) δ ppm: 1.35 (3H, doublet of doublets, J=7, 2 Hz); 2.52–2.65 (2H, multiplet); 3.01–3.08 (3H, multiplet); 3.51 (2H, triplet, J=11 Hz); 3.87 (1H, quartet, J=7 Hz); 4.16–4.23 (2H, multiplet); 4.99 (1H, doublet, J=4 Hz); 5.37 (2H, singlet); 5.85 (1H, doublet of doublets, J=15, 4 Hz); 6.58 (1H, doublet of doublets, J=15, 11 Hz); 6.74 (1H, doublet, J=16 Hz); 6.85–6.92 (2H, multiplet); 6.92 (1H, doublet of doublets, J=16, 11 Hz); 7.33 (1H, doublet of doublets, J=10, 1 Hz); 7.35–7.41 (2H, multiplet); 7.57 (1H, triplet, J=8 Hz); 7.93 (1H, singlet); 8.11 (1H, singlet).

IR spectrum $v_{max}$ (KBr) cm$^{-1}$: 2232, 1504, 1141, 1050.
Mass spectrum m/z (FAB): 614 (M$^+$+1).

EXAMPLE 14

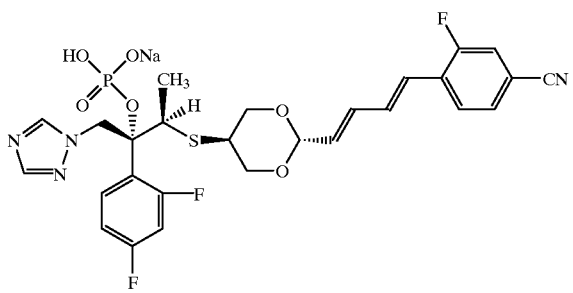

14(i) Diallyl [(1R,2R)-2-[[trans-2-[(1E,3E)-4-(4-cyano-2-fluorophenyl)-1,3-butadien-1-yl]-1,3-dioxan-5-yl]thio]-1-(2,4-difluorophenyl)-1-[(1H-1,2,4-triazol-1-yl)methyl]propyl]phosphite 490 mg (2.00 mmol) of bis(allyloxy)(diisopropylamino)phosphine [prepared as described in Tetrahedron Lett., 30, 4219 (1989)] were added to a suspension of 570 mg (1.00 mmol) of (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1yl)-2-butanol (prepared as described in Examples 1 or 4 above) and 350 mg (5.00 mmol) of tetrazole in 4 ml of a 1:1 mixture of acetonitrile and dichloromethane. The resulting mixture was stirred at ambient temperature for 15 hours. At the end of this time, the reaction mixture was concentrated and the resulting residue was dissolved in ethyl acetate. The solution thus obtained was washed with a saturated aqueous sodium hydrogen carbonate solution and with a saturated aqueous sodium chloride solution, dried over anhydrous magnesium sulfate and then concentrated under reduced pressure. The resulting oily residue was purified by chromatography on a silica gel (15 g) column using a 1:1 mixture of ethyl acetate and hexane as the eluant to give 609 mg (yield 89%) of the title compound as a colorless oil.

$^1$H-Nuclear magnetic resonance spectrum (400 MHz, CDCl$_3$) δ ppm: 1.29 (3H, doublet, J=7 Hz); 3.25 (1H, triplet of triplets, J=11, 5 Hz); 3.60–3.70 (3H, multiplet); 4.30–4.60 (6H, multiplet); 4.95 (1H, doublet, J=15 Hz); 5.08 (1H, doublet, J=4 Hz); 5.20–5.30 (2H, multiplet); 5.30–5.40 (3H, multiplet); 5.89 (1H, doublet of doublets, J=15, 4 Hz); 5.90–6.10 (2H, multiplet); 6.62 (1H, doublet of doublets, J=15, 10 Hz); 6.70–6.85 (2H, multiplet); 6.75 (1H, doublet, J=16 Hz); 6.95 (1H, doublet of doublets, J=16, 10 Hz); 7.30–7.45 (3H, multiplet); 7.58 (1H, triplet, J=8 Hz); 7.64 (1H, singlet); 8.19 (1H, singlet).

IR spectrum $v_{max}$ (CHCl$_3$) cm$^{-1}$: 2233, 1732, 1616, 1501.
Mass spectrum m/z (FAB): 687 (M$^+$+1).

14 (ii) Diallyl [(1R,2R)-2-[[trans-2-[(1E,3E)-4-(4-cyano-2-fluorophenyl)-1,3-butadien-1-yl-]-1,3-dioxan-5-yl]thio]-1-(2,4-difluorophenyl)-1-[(1H-1,2,4-triazol-1-yl)methyl]propyl]phosphate 0.42 ml of an approximately 5 M nonane solution of tert-butyl hydroperoxide were added to a solution of 530 mg (0.772 mmol) of diallyl [(1R,2R)-2-[[trans-2-[(1E,3E)-4-(4-cyano-2-fluorophenyl)-1,3-butadien-1-yl]-1,3-dioxan-5-yl]thio]-1-(2,4-difluorophenyl)-1-[(1H-1,2,4-triazol-1-yl)methyl]propyl]phosphite [prepared as described in Step 14(i) above] in 3 ml of dichloromethane at 0° C. The resulting mixture was stirred at 0° C. for 1 hour. At the end of this time, 5 ml of a saturated aqueous sodium thiosulfate solution were added to the reaction mixture and this mixture was stirred at ambient temperature for 1 hour. The reaction product was then extracted with ethyl acetate. The organic layer was washed with a saturated aqueous sodium chloride solution, dried over anhydrous magnesium sulfate and then concentrated under reduced pressure. The resulting residue was purified by chromatography on a silica gel (15 g) column using a 2:1 to 4:1 mixture of ethyl acetate and hexane as the eluant to afford 447 mg (yield 82%) of the title compound as a viscous colorless solid.

$^1$H-Nuclear magnetic resonance spectrum (400 MHz, CDCl$_3$) δ ppm: 1.29 (3H, doublet, J=7 Hz); 3.18 (1H, triplet of triplets, J=11, 5 Hz); 3.63 (2H, triplet of doublets, J=11, 2Hz); 3.79 (1H, quartet, J=7 Hz); 4.28 (1H, double doublet of doublets, J=11, 5, 2 Hz); 4.38 (1H, double doublet of doublets, J=11, 5, 2 Hz); 4.45–4.60 (2H, multiplet); 4.66 (2H, multiplet); 5.05 (1H, doublet, J=4 Hz); 5.08 (1H, doublet, J=15 Hz); 5.27 (1H, broad doublet, J=10 Hz); 5.31 (1H, broad doublet, J=10 Hz); 5.34 (1H, broad doublet, J=17 Hz); 5.43 (1H, broad doublet, J=17 Hz); 5.72 (1H, doublet, J=15 Hz); 5.88 (1H, doublet of doublets, J=15, 4 Hz);

5.85–6.05 (2H, multiplet); 6.61 (1H, doublet of doublets, J=15, 11 Hz); 6.75 (1H, doublet, J=16 Hz); 6.80–6.90 (2H, multiplet); 6.94 (1H, doublet of doublets, J=16, 11 Hz); 7.30–7.40 (3H, multiplet); 7.57 (1H, triplet, J=8 Hz); 7.69 (1H, singlet); 8.40 (1H, singlet).

IR spectrum $v_{max}$ (KBr) cm$^{-1}$: 2231, 1616, 1504, 1420.

Mass spectrum m/z (FAB): 703 (M$^+$+1).

14(iii) Diallyl [(1R,2R)-2-[[trans-2-[(1E,3E)-4-(4-cyano-2-fluorophenyl)-1,3-butadien-1-yl]-1,3-dioxan-5-yl]thio]-1-(2,4-difluorophenyl)-1-[(1H-1,2,4-triazol-1-yl)methyl]propyl]phosphate [Alternative to steps 14(i) and 14(ii)]

A suspension of 860 mg (1.52 mmol) of (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol (prepared as described in Examples 1 or 4 above) and 40 mg (1.67 mmol) of sodium hydride in 5 ml of dimethylformamide was stirred at ambient temperature for 10 minutes. 300 mg (1.53 mmol) of diallylphosphoryl chloride [prepared as described in Tetrahedron Lett., 28, 2259 (1987)] were added to the brown reaction mixture and the resulting mixture was then stirred at ambient temperature for 2 hours. At the end of this time the reaction mixture was diluted with ethyl acetate and the ethyl acetate solution was washed with a saturated aqueous sodium hydrogen carbonate solution and a saturated aqueous sodium chloride solution, dried over anhydrous magnesium sulfate and the concentrated under reduced pressure. The resulting residue was purified in the same manner as that described in Step 14(ii) above to afford 204 mg (yield 19%) of the title compound as a viscous colorless solid. The NMR, IR and mass spectral data were identical to those of the compound prepared in Step 14(ii) above.

14(iv) Sodium hydrogen [(1 R,2R)-2-[[trans-2-[(1E,3E)-4-(4-cyano-2-fluorophenyl)-1,3-butadien-1-yl]-1,3-dioxan-5-yl]thio-]-1-(2,4-difluorophenyl)-1-[(1H-1,2,4-triazol-1-yl)methyl]propyl]phosphate 1 mg of dichlorobis(triphenylphosphine)palladium (II) and 192 mg (0.66 mmol) of tributyltin hydride were added to a solution of 185 mg (0.263 mmol) of diallyl [(1R,2R)-2-[[trans-2-[(1E,3E)-4-(4-cyano-2-fluorophenyl)-1,3-butadien-1-yl]-1,3-dioxan-5-yl]thio]-1-(2,4-difluorophenyl)-1-[(1H-1,2,4-triazol-1-yl)methyl]propyl]phosphate [prepared as described in Steps 14(ii) or 14(iii) above] in 1.5 ml of dichloromethane. The resulting mixture was stirred at ambient temperature for 15 minutes. At the end of this time, hexane was added to the reaction mixture causing insoluble material to precipitate and the supernatant solution of this mixture was carefully removed by decantation. 3 ml of a saturated aqueous sodium hydrogen carbonate solution were added to a solution of the residue in 5 ml of methanol and the resulting mixture was stirred at ambient temperature for 15 hours. At the end of this time, the reaction mixture was concentrated under reduced pressure, methanol was added to the residue and the insoluble material was then removed by filtration. The filtrate was concentrated under reduced pressure. The resulting residue was purified by reverse phase chromatography on Cosmosil 75C$_{18}$-PREP (20 ml, product of Nacalai Tesque, Inc.) using a 3:2 mixture of methanol and water as the eluant. The collected fraction containing the desired product was concentrated and lyophilized to give 76 ml (yield 45%) of the title compound as a colorless solid.

$^1$H-Nuclear magnetic resonance spectrum (400 MHz, D$_2$O) δ ppm: 1.18 (3H, doublet, J=7 Hz); 2.89 (1H, multiplet); 3.40–3.60 (2H, m); 3.74 (1H, quartet, J=7 Hz); 3.97 (1H, multiplet); 4.14 (1H, multiplet); 5.05 (1H, doublet, J=6 Hz); 5.09 (1H, doublet, J=15 Hz); 5.39 (1H, doublet, J=15Hz); 5.73 (1H, doublet of doublets, J=15, 5 Hz); 6.52 (1H, doublet of doublets, J=15, 10 Hz); 6.70–6.80 (2H, multiplet); 6.74 (1H, doublet of doublets, J=16 Hz); 6.95 (1H, doublet of doublets, J=16, 11 Hz); 7.35–7.45 (2H, multiplet); 7.55–7.70 (2H, multiplet); 7.65 (1H, singlet); 8.69 (1H, singlet).

Mass spectrum $v_{max}$(KBr) cm$^{-1}$: 3417, 2232, 1616, 1498, 1418.

Mass spectrum m/z (FAB): 645 (M$^+$+1).

Reference Example 1

(2R,3R)-3-[[trans-2-[(1E,3E)-4-(4-Cyanophenyl)-1,3-butadien-1-yl]-1,3-dioxan-5-yl]thio]-2-(2,4-difluorolphenyl)-1-(1H-1,2,4-triazol-1-yl)-2-butanol Comparative Compound A

1(i) 4-[(1E,3E)-5-Oxo-1,3-pentadienyl]benzonitrile

A solution of 13.1 g (99 mmol) of 4-formylbenzonitrile (commercially available) and 40 g (120 mmol) of (triphenylphosphoranylidene)crotonaldehyde [prepared as described in Tetrahedron Lett., 493 (1971)] in 200 ml of dichloromethane was stirred at ambient temperature overnight. At the end of this time, the reaction mixture was concentrated to dryness in vacuo. The resulting residue was purified by chromatography on a silica gel (250 g) column using ethyl acetate as the eluant to give a mixture of the desired compound and a geometrical isomer thereof. A solution of the mixture of the two isomers in 150 ml of toluene was heated at reflux under irradiation with a tungsten lamp (300 W) for 12 hours. The reaction mixture was then concentrated in vacuo. The resulting residue was purified by chromatography on a silica gel (1.2 kg) column using a 1:9 mixture of ethyl acetate and toluene as the eluant to afford 3.46 g (yield 19%) of the title compound as pale brown needle-like crystals which were collected by filtration.

Melting point: 147–150° C.

$^1$H-Nuclear magnetic resonance spectrum (400 MHz, CDCl$_3$) δ ppm: 6.36 (1H, doublet of doublets, J=15, 8 Hz); 7.00 (1H, doublet, J=16 Hz); 7.09 (1H, doublet of doublets, J=16, 10 Hz); 7.27 (1H, doublet of doublets, J=15, 10 Hz); 7.59 (2H, doublet, J=8 Hz); 7.67 (2H, doublet, J=8 Hz); 9.67 (1H, doublet, J=8 Hz).

IR spectrum $v_{max}$ (KBr) cm$^{-1}$: 2226, 1683, 1670, 1626.

Mass spectrum m/z (EI): 183 (M$^+$, 100%), 154, 140, 127, 115.

Anal. calculated for C$_{12}$H$_9$NO: C, 78.67; H, 4.95; N,7.65. Found: C, 78.56; H, 5.05; N, 7.62.

1(ii) (2R,3R)-3-[[trans-2-[(1E,3E)-4-(4-Cyanophenyl)-1,3-butadien-1-yl]-1,3-dioxan-5-yl]thio]-2-(2,4-difluorophenyl)-1-(1H-1,2,4-triazol-1-yl)-2-butanol A mixture of 240 mg (1.31 mmol) of 4-[(1E,3E)-5-oxo-1,3-pentadienyl]benzonitrile [prepared as described in Step 1(i) above], 392 mg (1.09 mmol) of (2R,3R)-2-(2,4-difluorophenyl)-3-[[1-(hydroxymethyl)-2-hydroxyethyl]-thio]-1-(1H-1,2,4-triazol-1-yl)-2-butanol [prepared as described in Japanese Patent Application (Kokai) Hei 8-333350)], 249 mg (1.31 mmol) of p-toluenesulfonic acid monohydrate, 16 ml of dichloromethane and 3.9 g of molecular sieves 4A was stirred at ambient temperature over night. Aqueous sodium hydrogen carbonate was then added to the reaction mixture and insoluble material was removed by filtration. The resulting filtrate was extracted with ethyl acetate and the organic layer was dried and then concentrated. The resulting residue was purified by chromatography on silica gel (15 g) column using a 1:1 mixture of ethyl acetate and hexane as the eluant to give 465 mg (yield 81%) of the title compound as a solid. This solid was recrystallized from a mixture of ethyl acetate and hexane to afford crystals.

Melting point: 147–149° C.

$^1$H-Nuclear magnetic resonance spectrum (400 MHz, CDCl$_3$) δ ppm: 1.19 (3H, doublet, J=7 Hz); 3.33 (1H, quartet, J=7 Hz); 3.40 (1H, triplet of triplets, J=11, 5 Hz); 3.62 (1H, triplet, J=11 Hz); 3,64 (1H, triplet, J=11 Hz); 4.31 (1H, double doublet of doublets, J=11, 5, 2 Hz); 4.43 (1H, double doublet of doublets, J=11, 5, 2 Hz); 4.83 (1H, doublet, J=14 Hz); 5.00 (1H, singlet); 5.03 (1H, doublet, J=14 Hz); 5.06 (1H, doublet, J=4 Hz); 5.87 (1H, doublet of doublets, J=15, 4 Hz); 6.59 (1H, doublet of doublets, J=15, 10 Hz); 6.61 (1H, doublet, J=15 Hz); 6.7–6.8 (2H, multiplet); 6.87 (1H, doublet of doublets, J=15, 10 Hz); 7.35 (1H, triplet of doublets, J=8, 7 Hz); 7.48 (2H, doublet, J=8 Hz); 7.60 (2H, doublet, J=8 Hz); 7.79 (2H, singlet).

IR spectrum $ν_{max}$ (KBr)cm$^{-1}$: 2225, 1617, 1603, 1500, 1140 (KBr).

Mass spectrum m/z (FAB): 525 (M$^+$+1).

Specific rotation: $[α]_D^{25}$-73.4° (c=1.30, CHCl$_3$).

Anal. calculated for C$_{27}$H$_{26}$F$_2$N$_4$O$_3$S: C, 61.82; H, 5.00; N,10.68 Found: C, 62.00; H, 5.01; N, 10.56.

Reference Example 2

(2R,3R)-4-[[trans-2-[(1E,3E)-4-(4-Cyano-2-fluorophenyl)-1,3-butadien-1-yl]-1,3-dioxan-5-yl]-2-(2,4-difluorophenyl)-3-methyl-1-(1H-1,2,4-triazol-1-yl)-2-butanol Comparative Compound C Using the procedure described in Example 1(iii) above, a reaction was carried out using 708 mg (3.51 mmol) of 3-fluoro-4-[(1E,3E)-5-oxo-1,3-pentadienyl]-benzonitrile [prepared as described in Example 1(ii) above] and 1000 mg (2.93 mmol) of (4S,5R)-5-(2,4-difluorophenyl)-2-(hydroxymethyl)-4-methyl-6-(1H-1,2,4-triazol-1-yl)-1,5-hexanediol [prepared as described in Japanese Patent Application (Kokai) Hei 11-80135]. The crude extract was purified by chromatography on a silica gel (20 g) column using a 1:1 mixture of ethyl acetate and hexane as the eluant to give 1.18 g (yield 77%) of the title compound as a pale non-crystalline solid.

$^1$H-Nuclear magnetic resonance spectrum (270 MHz, CDCl$_3$) δ ppm: 0.83 (3H, doublet, J=7 Hz); 1.09 (1H, multiplet); 1.43 (1H, multiplet); 1.95–2.20 (2H, multiplet); 3.45 (1H, triplet, J=11 Hz); 3,47 (1H, triplet, J=11 Hz); 4.11 (1H, double doublet of doublets, J=11, 5, 2 Hz); 4.23 (1H, double doublet of doublets, J=11, 5, 2 Hz); 4.48 (1H, doublet, J=14 Hz); 4.86 (1H, singlet); 4.94 (1H, doublet, J=14 Hz); 5.03 (1H, doublet, J=4 Hz); 5.91 (1H, doublet of doublets, J=15, 4 Hz); 6.61 (1H, doublet of doublets, J=15, 10 Hz); 6.65–6.80 (3H, multiplet); 6.95 (1H, doublet of doublets, J=15, 10 Hz); 7.33 (1H, doublet of doublets, J=10, 1 Hz); 7.35–7.45 (1H, multiplet); 7.39 (1H, doublet of doublets, J=8, 1 Hz); 7.57 (1H, triplet, J=8 Hz); 7.77 (1H, singlet); 7.87 (1H, singlet).

IR spectrum $ν_{max}$ (KBr) cm$^{-1}$: 2231, 1615, 1499, 1141.

Mass spectrum m/z (EI): 524 (M$^+$, 100%), 368, 224.

Specific rotation: $[α]_D^{25}$-66° (c=0.5. CHCl$_3$).

Formulation Examples

Formulation Example 1

Hard Capsules

The components shown below were mixed in the quantities shown below to give the composition shown below which was then used to fill a standard two-component hard gelatin capsule. after which the capsule was washed and dried to give the desired hard capsule.

| | |
|---|---|
| Powdered compound (Ib) | 100 mg |
| Lactose | 150 mg |
| Cellulose | 50 mg |
| Magnesium stearate | 6 mg |
| | 306 mg |

Formulation Example 2

Soft Capsules

A mixture of compound (Ib) in a digestible oil such as soy bean oil, cottonseed oil or olive oil is prepared and is injected into gelatin to obtain a soft capsule containing 100 mg of the active ingredient which is then washed and dried to give the desired soft capsule.

Formulation Example 3

Tablets

Tablets having the composition indicated below are produced in accordance with a conventional method.

| | |
|---|---|
| Compound (Ib) | 100 mg |
| Colloidal silicon dioxide | 0.2 mg |
| Magnesium stearate | 5 mg |
| Microcrystalline cellulose | 275 mg |
| Starch | 11 mg |
| Lactose | 98.8 mg |
| | 490 mg |

If desired, the tablets can be coated with a suitable preparation coating.

Test Examples

Test Example 1

In vitro Antifungal Activity

The antifungal activities of test compounds were assessed according to their minimum inhibitory concentrations (MICs) which were measured by the methods described below.

1(i) Measurement Method for Candida Species

A modified version of the procedure described in Japanese Journal of Medical Mycology, 36, 62 (1995) was used, MICs being determined by the broth microdilution method. Each test compound was dissolved in dimethyl sulfoxide (DMSO). Serial two-fold dilutions of each compound were prepared with DMSO and then final dilutions were prepared with RPMI1640 medium (product of Dainippon Pharmaceutical Co., Ltd.) which was buffered to pH 7.0 with 0.165 M 3-(morpholino)propanesulfonic acid (MOPS). The final concentration of DMSO did not exceed 1%. Colonies of the test fungi were suspended in physiological saline followed by adjustment to $5.0 \times 10^2$ to $2.5 \times 10^3$ cells/ml with RPMI1640 medium which was buffered to pH 7.0 with 0.165 M MOPS. 100 µl of the fungal suspension were added to each of the wells of microtitre plates and then 100 µl of each diluted test compound were added to one of said wells and mixed with the fungal suspension therein, before incubating at 35° C. for 24–72 hours. When obvious growth was observed in the compound-free control wells, the MICs were determined for each test compound. The MICs were defined as the lowest compound concentrations causing at least 80% growth inhibition when compared with the control.

1(ii) Measurement Method for *Cryptococcus neoformans*

A modified version of the Broth Dilution Antifungal Susceptibility Testing of Yeast; Approved Standard M27-A (Vol. 17, No. 9, June 1997, NCCLS) was used. MICs being determined by the broth microdilution method. Each test compound was dissolved in DMSO. Serial two-fold dilutions of each compound were prepared with DMSO and final dilutions were prepared with yeast nitrogen base medium (product of Difco Laboratories) buffered to pH 7.0 with 0.165 M MOPS. The final concentration of DMSO did not exceed 1%. Colonies of the test fungi were suspended in physiological saline followed by adjustment to $5.0 \times 10^3$ to $2.5 \times 10^4$ cells/ml with yeast nitrogen base medium buffered to pH 7.0 with 0.165 M MOPS. 100 µl of the fungal suspension were added to each of the wells of microtitre plates and then 100 µl of each diluted test compound were added to one of said wells and mixed with the fungal suspension therein, before incubating at 35° C. for 48–72 hours. When obvious growth was observed in the compound-free control wells, the MICs were determined for each test compound. The MICs were defined as the lowest compound concentrations causing at least 50% growth inhibition when compared with the control as measured by light absorbance at 485 nm.

1(iii) Measurement Method for Aspergillus Species

A modified version of the protocol in Antimicrob. Agents Chemother., 39, 314 (1995) was used, MICs being determined by the broth microdilution method. Test compounds were dissolved in dimethyl sulfoxide (DMSO). Serial two-fold dilutions of each compound were prepared with DMSO and then final dilutions were prepared with RPMI1640 medium (product of Dainippon Pharmaceutical Co., Ltd.) buffered to pH 7.0 with 0.165 M MOPS. The final concentration of DMSO did not exceed 1%. Colonies of the test fungi were suspended in physiological saline followed by adjustment to about $1.0 \times 10^4$ cells/ml with RPMI1640 medium buffered to pH 7.0 with 0.165 M MOPS. 100 µl of the fungal suspension were added to each of the wells of microtitre plates and then 100 µl of each diluted test compound were added to one of the wells and mixed with the fungal suspension therein, before incubating at 30° C. for 24–72 hours. When obvious growth was observed in the compound-free control wells, the MICs were determined for each test compound. The MICs were defined as the lowest compound concentrations causing at least 80% growth inhibition when compared with the control.

The compound of formula (Ib) of the present invention was tested for in vitro activity using the above tests and its activity compared with that of Comparative Compound A (prepared as described in Reference Example 1 above) and Comparative Compound B (prepared according to Example 27 of Japanese Patent Application (Kokai) Hei 8-333350), the structures of which are shown below. Comparative Compounds A and B are compounds disclosed in Japanese Patent Application (Kokai) No. Hei 8-333350 and EP-A-0841327. The results were as shown in Table 1.

Comparative Compounds A and B are represented by the following formulae:

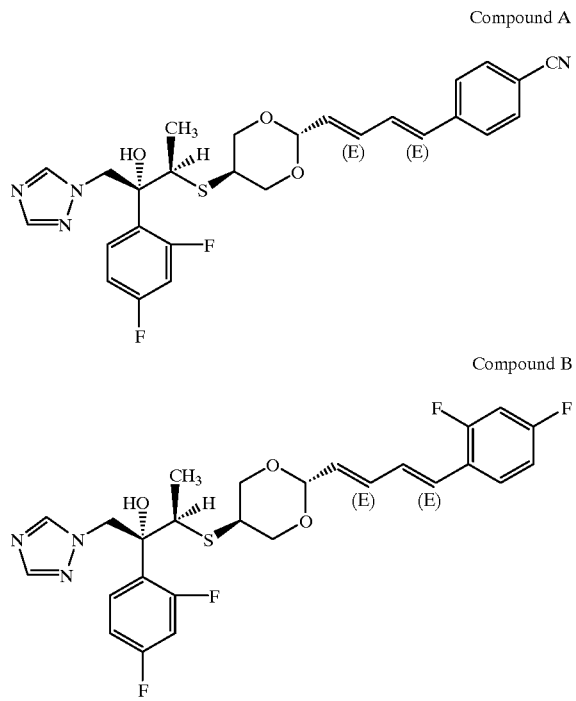

TABLE 1

| | Antifungal Activity in vitro MIC value (µg/ml) | | | | |
|---|---|---|---|---|---|
| Compound | C.a. (1)[b] | C.a. (2)[c] | C.a. (3)[d] | C.n.[e] | A.f.[f] |
| Compound (Ib) | 0.25 | ≦0.008 | 0.063 | ≦0.008 | 0.031 |
| Comparative Compound (A) | 0.5 to 1 | 0.016 | 0.125 to 0.25 | 0.016 | 0.031 |
| Comparative Compound (B) | 0.5 | 0.031 to 0.063 | 0.125 to 0.25 | ≦0.008 | 0.125 |

The test microorganisms of [b] through [f] are as indicated below.
[b]C.a. (1): Canadida albicans ATCC 64550.
[c]C.a. (2): Canadida albicans TIMM 3164.
[d]C.a. (3): Canadida albicans TIMM 3165.
[e]C.n.: Cryptococcus neoformans TIMM 0362.
[f]A.f.: Aspergillus fumigatus SANK 10569.

As can be seen from Table 1, the compound of formula (Ib) of the present invention demonstrated in vitro antifungal activity that was equal to or better than that of Comparative Compounds A and B described in Japanese Patent Application (Kokai) No. Hei 8-333350 and EP-A-0841327.

Test Example 2

Acid Stability Test

The stability of the compounds of the present invention in the presence of acid was assessed according to their half-life ($t_{1/2}$) in an acidic solution as measured by the method described below.

700 μl of 0.01 N (pH 2.0) hydrochloric acid were added to a solution of a test compound (the concentration of the test compound was 167 μg/ml) in 300 μl of acetonitrile to give a mixture in which the initial concentration of the test compound was 50 μg/ml and the acetonitrile content was 30%, followed by incubation of the mixture at 37° C. A small amount of the solution was taken from the reaction solution at predetermined time intervals and the reaction was stopped in these samples by neutralizing with an aqueous sodium hydroxide solution. Quantitative determination of the residual rate of the test compound in the solution was determined by HPLC.

The half-life ($t_{1/2}$) of the test compound in 0.01 N HCl was determined according to the following equation using the degradation rate constant $k_{deg}$ which was determined by semi-logarithmic regression analysis of the residual rate in the solution.

$t_{1/2} = (\ln 2)/k_{deg}$

The larger the $t_{1/2}$ value of the compound, the higher is its acid stability.

The results obtained for the compound of formula (Ib) of the present invention and those for Comparative Compound A, Comparative Compound B and Comparative Compound C (which is disclosed in Japanese Patent Application (Kokai) Hei 11-80135 and WO-A-99/02524 and is prepared as described in Reference Example 2 above) are shown in Table 2 below.

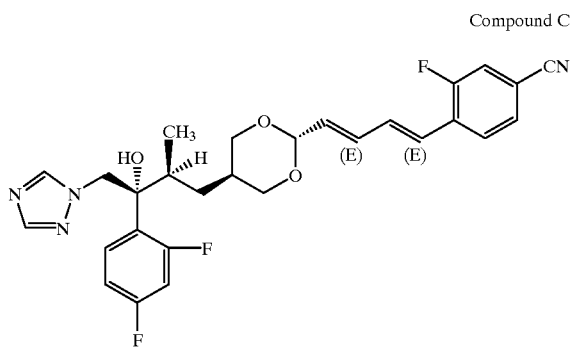

Compound C

TABLE 2

Stability in Acidic Solution

| Compound | t½ (min) |
|---|---|
| Compound (Ib) | 6.40 |
| Comparative Compound (A) | 3.12 |
| Comparative Compound (B) | 1.54 |
| Comparative Compound (C) | 2.42 |

The compound of formula (Ib) of the present invention demonstrated stability in the presence of acid that was superior to that of Comparative Compounds A, B and C.

Test Example 3

Oral Absorption Rate

The oral absorption rate of the compounds of the present invention was assessed according to the bioavailability (BA) of said compounds as measured by the method described below.

A test compound in polyethylene glycol 400 (PEG 400) was administered either orally (4 animals) or intravenously into the caudal vein (3 animals) of SD rats (age 7 weeks) which had fasted overnight. The oral dose of the test compound was 20 mg per kg of rat body weight. The intravenous dose of the test compound injected into the caudal vein was 2 mg per kg of rat body weight. The amount of PEG 400 used was 1 ml per kg of rat body weight for both oral and intravenous administration. The bioavailability (BA) values were calculated according to the following equation using the integrated values of the blood concentration of the test compound up to 48 hours after oral administration [$AUC_{po}$(0–48 h)], and the integrated values of the blood concentration extrapolated from 0 to infinite time after intravenous administration into the caudal vein [$AUC_{iv}$(0–∞)].

$BA (\%) = \{[(AUC_{po}(0-48))/(dose_{po})]/[(AUC_{iv}(0-\infty))/(dose_{iv})]\} \times 100$ The larger the value of BA, the higher the oral absorption rate. The results for the compound of formula (Ib) of the present invention and those for Comparative Compounds A, B and C are shown in Table 3.

TABLE 3

Bioavailability

| Compound | BA (%) |
|---|---|
| Compound (Ib) | 123 |
| Comparative Compound (A) | 50.7 |
| Comparative Compound (B) | 6.24 |
| Comparative Compound (C) | 57.8 |

The compound of formula (Ib) of the present invention demonstrated an oral absorption rate that was superior to Comparative Compounds A, B and C.

The results above show that the compounds of formula (1b) and the pharmaceutically acceptable esters and salts thereof of the present invention demonstrate a superior in vitro and in vivo antifungal activity, acid stability and oral absorption rate as compared with the compounds described in Japanese Patent Application (Kokai) Hei 8-333350 and Japanese Patent Application (Kokai) Hei 11-80135. The compounds of the present invention also show low toxicity.

The compounds of formula (I) and the pharmaceutically acceptable esters and salts thereof of the present invention are particularly useful as antifungal agents against a wide range of eumycetes.

What is claimed is:

1. A method for the prophylaxis or treatment of fungal infections in a mammal which comprises administering to said mammal an effective amount of a compound having antifungal activity, wherein said compound having antifungal activity is a compound of the following formula (I) or a pharmaceutically acceptable ester or salt thereof:

(I)

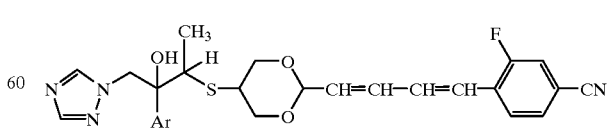

wherein Ar is a phenyl group which may optionally be substituted by from 1 to 3 substituents selected from the group consisting of halogen atoms and trifluoromethyl groups.

2. A method for the prophylaxis or treatment of fungal infections according to claim 1, wherein said mammal is a human.

3. A method for the prophylaxis or treatment of fungal infections according to claim 2, comprising administering to said mammal a compound of formula (I) or a pharmaceutically acceptable ester or salt thereof wherein Ar is a 2,4-difluorophenyl group or 2-fluorophenyl group.

4. A method for the prophylaxis or treatment of fungal infections according to claim 2, comprising administering to said mammal a compound of formula (I) or a pharmaceutically acceptable ester or salt thereof wherein Ar is a 2,4-difluorophenyl group.

5. A method for the prophylaxis or treatment of fungal infections according to claim 2, comprising administering to said mammal a compound of formula (I) or a pharmaceutically acceptable ester or salt thereof, wherein said compound of formula (I) is a compound of the following formula (Ia):

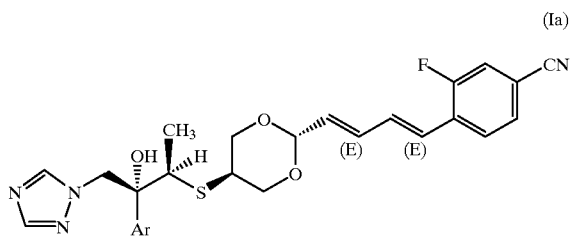

wherein Ar is a phenyl group which may optionally be subtituted by from 1 to 3 substituents selected from the group consisting of halogen atoms and trifluoromethyl groups.

6. A method for the prophylaxis or treatment of fungal infections according to claim 2, comprising administering to said mammal (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol or a pharmaceutically acceptable ester or salt thereof.

7. A method for the prophylaxis or treatment of fungal infections according to claim 2, comprising administering to said mammal (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol.

8. A method for the prophylaxis or treatment of fungal infections according to claim 2, comprising administering to said mammal (2R,3R)-3-[[trans-2-[(1E,3E)-4-(4-cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol in crystalline form.

9. A method for the prophylaxis or treatment of fungal infections according to claim 2, comprising administering to said mammal (2R,3R)-3-[[trans-2-[(1E,3E)-4-(4-Cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol in crystalline form, in which said crystals have main peaks at lattice distances of 3.14, 3.39, 3.71, 3.75, 4.21, 4.88, 5.28, 5.42, 5.89, 5.95, 6.79, 6.86, 8.03 and 8.41 Å determined by X-ray diffraction by the powder method using the copper $K_\alpha$ ray.

10. A method for the prophylaxis or treatment of fungal infections according to claim 2, comprising administering to said mammal (2R,3R)-3-[[trans-2-[(1E,3E)-4-(4-Cyano-2-fluorophenyl)-1,3-butadien-1-yl]-1,3-dioxan-5-yl]thio]-2-(2,4-difluorophenyl)-1-(1H-1,2,4-triazol-1-yl)-2-butanol in crystalline form, in which said crystals have main peaks at lattice distances of 3.62, 3.96, 4.54, 4.59, 4.79, 4.91, 5.32, 5.48, 6.18, 7.99, and 15.93 Å determined by X-ray diffraction by the powder method using the copper $K_\alpha$ ray.

11. A method for the prophylaxis or treatment of fungal infections according to claim 5 wherein said mammal is a human.

12. A method for the prophylaxis or treatment of fungal infections according to claim 6 wherein said mammal is a human.

13. A method for the prophylaxis or treatment of fungal infections according to claim 7 wherein said mammal is a human.

14. A method for the prophylaxis or treatment of fungal infections according to claim 8 wherein said mammal is a human.

15. A method for the prophylaxis or treatment of fungal infections according to claim 9 wherein said mammal is a human.

16. A method for the prophylaxis or treatment of fungal infections according to claim 10 wherein said mammal is a human.

* * * * *